US009969977B2

(12) United States Patent
Ho et al.

(10) Patent No.: US 9,969,977 B2
(45) Date of Patent: *May 15, 2018

(54) CELL POPULATIONS WHICH CO-EXPRESS CD49C AND CD90

(75) Inventors: Tony W. Ho, Berwyn, PA (US); Gene C. Kopen, Wynnewood, PA (US); William F. Righter, Ridley Park, PA (US); J. Lynn Rutkowski, Wynnewood, PA (US); Joseph Wagner, West Chester, PA (US); W. Joseph Herring, Valley Forge, PA (US); Vanessa Ragaglia, Newtown Square, PA (US)

(73) Assignee: GARNET BIOTHERAPEUTICS, Malvern, PA (US)

( * ) Notice: Subject to any disclaimer, the term of this patent is extended or adjusted under 35 U.S.C. 154(b) by 4139 days.

This patent is subject to a terminal disclaimer.

(21) Appl. No.: 10/251,685

(22) Filed: Sep. 20, 2002

(65) Prior Publication Data

US 2004/0058412 A1   Mar. 25, 2004

(51) Int. Cl.
C12N 5/077 (2010.01)
C12N 5/078 (2010.01)
A61K 35/12 (2015.01)

(52) U.S. Cl.
CPC ......... *C12N 5/0657* (2013.01); *C12N 5/0634* (2013.01); *A61K 35/12* (2013.01); *C12N 2501/06* (2013.01); *C12N 2501/405* (2013.01); *C12N 2506/11* (2013.01)
USPC ........................... 435/366; 435/325; 435/374

(58) Field of Classification Search
None
See application file for complete search history.

(56) References Cited

U.S. PATENT DOCUMENTS

| | | |
|---|---|---|
| 4,608,199 A | 8/1986 | Caplan et al. |
| 4,609,551 A | 9/1986 | Caplan et al. |
| 4,620,327 A | 11/1986 | Caplan et al. |
| 4,728,641 A | 3/1988 | Tubaro et al. |
| 5,061,620 A | 10/1991 | Tsukamoto et al. |
| 5,197,985 A | 3/1993 | Caplan et al. |
| 5,226,914 A | 7/1993 | Caplan et al. |
| 5,486,359 A | 1/1996 | Caplan et al. |
| 5,591,625 A | 1/1997 | Gerson et al. |
| 5,643,736 A | 7/1997 | Bruder et al. |
| 5,716,616 A | 2/1998 | Prockop et al. |
| 5,728,581 A | 3/1998 | Schwartz et al. |
| 5,733,542 A | 3/1998 | Haynesworth et al. |
| 5,736,396 A | 4/1998 | Bruder et al. |
| 5,811,094 A | 9/1998 | Caplan et al. |
| 5,837,539 A | 11/1998 | Caplan et al. |
| 5,855,619 A | 1/1999 | Caplan et al. |
| 5,942,225 A | 8/1999 | Bruder et al. |
| 5,962,323 A | 10/1999 | Greenberger et al. |
| 6,010,696 A | 1/2000 | Caplan et al. |
| 6,087,113 A | 7/2000 | Caplan et al. |
| 6,174,333 B1 | 1/2001 | Kadiyala et al. |
| 6,184,035 B1 | 2/2001 | Csete et al. |
| 6,653,134 B2 | 11/2003 | Prockop et al. |
| 6,719,972 B1 | 4/2004 | Gribben et al. |
| 6,974,571 B2 | 12/2005 | Prockop et al. |
| 7,015,037 B1 * | 3/2006 | Furcht et al. ................. 435/372 |
| 7,056,738 B2 | 6/2006 | Prockop et al. |
| 7,521,465 B2 | 4/2009 | Nag et al. |
| 2001/0034061 A1 | 10/2001 | Csete et al. |
| 2001/0036642 A1 | 11/2001 | Asselineau et al. |
| 2002/0058025 A1 | 5/2002 | Prockop et al. |
| 2002/0146821 A1 | 10/2002 | Sanchez-Ramos et al. |
| 2002/0168765 A1 | 11/2002 | Prockop et al. |
| 2003/0003090 A1 | 1/2003 | Prockop et al. |
| 2003/0003572 A1 | 1/2003 | Anderson et al. |
| 2003/0003574 A1 | 1/2003 | Toma et al. |

(Continued)

FOREIGN PATENT DOCUMENTS

| | | |
|---|---|---|
| WO | WO 99/43286 | 9/1999 |
| WO | WO 00/24261 | 5/2000 |

(Continued)

OTHER PUBLICATIONS

Clayton et al. (J. Am Soc. Nephrol, 1997: 8(4): 604-15)-Abtract only.*
Silva et al. (Stem Cells, 2003, 21: 661-669).*
Santalucia et al. (Cardiovascular Research, 2003, 59: 639-648).*
Rithidech et al. (Blood Cells, Molecules, Diseases, 2001, 27(2): 496-504).*
Koller et al. (Annals New York Academy of Sciences, 1992, 665: 105-116).*
Baksh et al. J Cell Mol Med vol. 8, No. 3, 2004 pp. 301-316.*
Chamberlain et al. Stem Cells 2007; 25; 2739-2749.*
Lodie et al Tissue Engineering vol. 8, No. 5, 2002, pp. 739-751.*
Kolf et al Arthritis Research & Therapy 9:204 2007.*
Akiyomo, Y., et al., "Functional Repair of Demyelinated Spinal Cord Axons in the Adult Rat by Transplantation of Clonal Neural Stem Cells Derived From Adult Human Brain," *Society for Neuroscience* 25: Abstract 86.9 (1999).
Ashhurst, D.E., et al., "The Collagens and Glycosaminoglycans of the Extracellular Matrices Secreted by Bone Marrow Stromal Cells Cultured In Vivo in Diffusion Chambers," *J. Orthoped. Res.* 8(5):741-749 (1990).

(Continued)

*Primary Examiner* — Renee Claytor
(74) *Attorney, Agent, or Firm* — Cynthia M. Bouchez; Medler Ferro Woodhouse & Mills PLLC

(57) ABSTRACT

Substantially homogenous cells populations which co-express CD49c, CD90 and telomerase are made. In one embodiment, humans suffering from a degenerative, traumatic, acute injury, cardiac or neurological condition are treated with the substantially homogenous cells populations which co-express CD49c, CD90 and telomerase. In another embodiment, committed progenitor cells are made are made by selecting from a cultured source of a cell population which co-express CD49c and CD90 and modifying the cell population. The committed progenitor cells can be employed to treat a human suffering from a degenerative, traumatic, acute injury, cardiac or neurological condition and to formulate pharmaceutical compositions. In a further embodiment, a substantially homogenous population of cells which co-express CD49c, CD90 and at least one cardiac-related transcription factor is made and can be used to treat a human suffering from a cardiac condition.

16 Claims, 10 Drawing Sheets

(56) References Cited

U.S. PATENT DOCUMENTS

| | | |
|---|---|---|
| 2003/0017587 A1 | 1/2003 | Rader et al. |
| 2003/0039639 A1 | 2/2003 | Prockop et al. |
| 2003/0059412 A1 | 3/2003 | Prockop et al. |
| 2003/0059414 A1* | 3/2003 | Ho et al. .................... 424/93.21 |
| 2003/0059941 A1 | 3/2003 | Prockop et al. |
| 2003/0202966 A1 | 10/2003 | Prockop et al. |
| 2003/0203484 A1 | 10/2003 | Black et al. |
| 2004/0033214 A1 | 2/2004 | Young et al. |
| 2004/0091464 A1 | 5/2004 | Prockop et al. |
| 2004/0107453 A1 | 6/2004 | Furcht et al. |
| 2004/0166097 A1 | 8/2004 | Prockop et al. |
| 2004/0208861 A1 | 10/2004 | Prockop et al. |
| 2005/0181502 A1 | 8/2005 | Furcht et al. |
| 2005/0233452 A1 | 10/2005 | Ho et al. |
| 2005/0283844 A1 | 12/2005 | Furcht et al. |
| 2006/0008450 A1 | 1/2006 | Verfaillie et al. |
| 2006/0030041 A1 | 2/2006 | Furcht et al. |
| 2006/0288431 A1 | 12/2006 | Nakatsuji et al. |
| 2007/0224177 A1 | 9/2007 | Ho et al. |
| 2007/0231309 A1 | 10/2007 | Ho et al. |
| 2007/0264232 A1 | 11/2007 | Ho et al. |
| 2008/0119946 A1 | 5/2008 | Nugent et al. |
| 2009/0053183 A1 | 2/2009 | Kopen et al. |

FOREIGN PATENT DOCUMENTS

| | | |
|---|---|---|
| WO | WO 00/69448 | 11/2000 |
| WO | WO 01/04268 A1 | 1/2001 |
| WO | WO 01/11011 A2 | 2/2001 |
| WO | WO 01/34167 A1 | 5/2001 |
| WO | WO 01/59072 A1 | 8/2001 |
| WO | WO 01/78753 | 10/2001 |
| WO | WO 02/18401 A2 | 3/2002 |
| WO | WO 02/34889 | 5/2002 |
| WO | WO 03/025149 A2 | 3/2003 |
| WO | WO 2008/156728 A1 | 12/2008 |

OTHER PUBLICATIONS

Ashton, B.A., et al., "Formation of Bone and Cartilage by Marrow Stromal Cells in Diffusion Chambers in Vivo," *Clinical Orthopaedics and Related Research*, 151:294-307 (1990).

Ashton, B.A., et al., "Distribution of Fibroblastic Colony-Forming Cells in Rabbit Bone Marrow and Assay of their Osteogenic Potential by an in vivo Diffusion Chamber Method," *Calcif. Tissue Int.* 36:83-86 (1984).

Azizi, S. A., et al., "Engraftment and Migration of Human Bone Marrow Stromal Cells Implanted in the Brains of Albino Rats-Similarities to Astrocyte Grafts," *Proc. Natl. Acad. Sci. USA* 95: 3908-3913 (1998).

Azizi, S. A., "Exploiting NonNeural Cells to Rebuild the Nervous System: From Bone Marrow to Brain," *The Neuroscientist* 6(5): 353-361.

Bab, I., et al., "Assessment of an in vivo Diffusion Chamber Method as a Quantitative Assay for Osteogenesis," *Calcif. Tissue Int.* 36:77-82 (1984).

Bab, I., et al., "Osteogenesis in in vivo diffusion chamber cultures of human marrow cells," *Bone and Mineral*, 4:373-386 (1988).

Bab, I., et al., "Ultrastructure of Bone and Cartilage Formed in Vivo in Diffusion Chambers," *Clinical Orthopaedics and Related Research*, 187:243-254 (1984).

Bianco, P., et al., "Bone Marrow Stromal Stem Cells: Nature, Biology, and Potential Applications," *Stem Cells* 19: 180-192 (2001).

Benayahu, D., et al., "Bone Marrow-Derived Stromal Cell Line Expressing Osteoblastic Phenotype in Vitro and Osteogenic Capacity In Vivo," *J. of Cell. Physiol.* 140:1-7 (1989).

Budenz, R.W., et al., "Osteogenesis and Leukopoieses Within Diffusion- Chamber Implants of Isolated Bone Marrow Subpopulations," *Am. J. Anat.* 159:455-474 (1980).

Chopp, M., et al., "Spinal Cord Injury in Rat: Treatment with Bone Marrow Stromal Cell Transplantation," *NeuroReport* 11(13): 3001-3005 (2000).

Colter, D. C., et al., "Rapid Expansion of Recycling Stem Cells in Cultures of Plastic-Adherent Cells from Human Bone Marrow," *Proc. Natl. Acad. Sci. USA* 97(7): 3213-3218 (2000).

Coyle, A.J., et al., "Human Mesenchymal Stomal Cells Can Differentiate into Oligodendrocyte Lineage in Transplantation Experiments with MD Rats,"*Soc. for Neurosci.* 26: Abstract 415.11 (2000).

Diduch, D.R., et al, "Two Cell Lines from Bone Marrow that Differ in Terms of Collagen Synthesis, Osteogenic Characteristics, and Matrix Mineralization," *J. of Bone & Joint Surgery* 75:92-105 (1993).

Eglitis, M. A., et al., "Hematopoietic Cells Differentiate into Both Microglia and Macroglia in the Brains of Adult Mice," *Proc. Natl. Acad. Sci. USA* 94: 4080-4085 (1997).

Ferrari, G., et al., "Muscle Regeneration by Bone Marrow-Derived Myogenic Progenitors," *Science* 279: 1528-1530 (1998).

Friedenstein, A.J., et al., "Bone Marrow Osteogenic Stem Cells: in Vitro cultivation and Transplantation in Diffusion Chambers," *Cell Tissue Kinet.* 20:263-272 (1987).

Gundle, R., et al., "Human Bone Tissue Formation in Diffusion Chamber Culture in Vivo by Bone-Derived Cells and Marrow Stromal Fibroblastic Cells," *Bone* 16(6):597-601 (1995).

Haynesworth, S.E., et al., "Cell Surface Antigens on Human Marrow-Derived Mesenchymal Cells are Detected by Monoclonal Antibodies," *Bone* 13:69-80 (1992).

Haynesworth, S.E., et al., "Characterization of Cells with Osteogenic Potential from Human Marrow," *Bone* 13:81-88 (1992).

Himes, B. T., et al., "Grafting Human Bone Marrow Stromal Cells into Injured Spinal Cord of Adult rats," *Society for Neuroscience* 25: Abstract 86.11 (1999).

Kataoka, H., et al., "Transplant of Bone Marrow and Muscle-Derived Connective Tissue Cultures in Diffusion Chambers for Bioassay of Bone Morphogenetic Protein," *Clinical Orthopaedics and Related Research* 286:262-270 (1993).

Kopen, G. C., et al., "Marrow Stromal Cells Migrate Throughout Forebrain and Cerebellum, and They Differentiate into Astrocytes After Injection into Neonatal Mouse Brains," *Proc. Natl. Acad. Sci. USA* 96: 10711-10716 (1999).

Krebsbach, P.H., et al., "Bone Formation In Vivo: Comparison of Osteogenesis by Transplanted Mouse and Human Marrow Stromal Fibroblasts," *Transplantation* 63(8):1059-1069 (1997).

Lennon, D.P., et al., "Cultivation of Rat Marrow-Derived Mesenchymal Stem Cells in Reduced Oxygen Tension: Effects on In Vitro and In Vivo Osteocndrogenesis," *J. of Cell. Physiol.* 187:345-355 (2001).

Li, J., et al., "Nontransformed Colony-Derived Stromal Cell Lines from Normal Human Marrows. II. Phenotypic Characterization and Differentiation Pathway," *Experimental Hematology* 23: 133-141 (1995).

Liechty, K. W., et al., "Human Mesenchymal Stem Cells Engraft and Demonstrate Site-Specific Differentiation after In Utero Transplantation in Sheep," *Nature Medicine* 6(11): 1282-1286 (2000).

Majumdar, M .K., et al., "Phenotypic and Functional Comparison of Cultures of Marrow-Derived Mesenchymal Stem Cells (MSCs) and Stromal Cells," *J. Cell. Physiol.* 176: 57-66 (1998).

Mardon, H.J., et al., "Development of Osteogenic Tissue in Diffusion Chambers from Early Precursor Cells in Bone Marrow of Adult Rats," *Cell Tissue Research*, 250:157-165 (1987).

Pereira, M. K., et al., "Cultured Adherent Cells from Marrow Can Serve as Long-Lasting Precursor Cells for Bone, Cartilage, and Lung in Irradiated Mice," *Proc. Natl. Acad. Sci. USA* 92: 4857-4861 (1995).

Phinney, D. G., et al., "Donor Variation in the Growth Properties and Osteogenic Potential of Human Marrow Stromal Cells," *J. Cell. Biochem.* 75: 424-436 (1999).

Phinney, D. G., et al., "Plastic Adherent Stromal Cells From the Bone Marrow of Commonly Used Strains of Inbred Mice: Variations in Yield, Growth, and Differentiation," *J. Cell. Biochem.* 72: 570- 585, (1999).

Pittenger, M. F., et al., "Multilineage Potential of Adult Human Mesenchymal Stem Cells," *Science* 284: 143-147 (1999).

Prockop, D. J., "Marrow Stromal Cells as Stem Cells for Nonhematopoietic Tissues," *Science* 276: 71-74 (1997).

(56) References Cited

OTHER PUBLICATIONS

Quinones, R.R., "Hematopoietic Engraftment and Graft Failure After Bone Marrow Transplantation," *Am. J. of Pediatric Hematology/Oncology* 15(1):3-17 (1993).
Roisen, F. J., et al., "Murine and Human Adult Olfactory Neuroepithelial Stem Cells," *Society for Neuroscience* 26: Abstract 312.7 (2000).
Sanchez-Ramos, J., et al., "Adult Bone Marrow Stromal Cells Differentiate into Neural Cells in Vitro," *Experimental Neurology* 164: 247-256 (2000).
Sanchez-Ramos, J., et al., "Bone Marrow Stromal Cells Grafted into Adult Rat Brain Migrate, Organize in Architectonic Patterns and Express Neuronal Markers," *Neurology* 52: A14, S06.001 (1999).
Schwarz, E. J., et al., "Multipotential Marrow Stromal Cells Transduced to Produce L-DOPA: Engraftment in a Rat Model of Parkinson Disease," *Human Gene Therapy* 10: 2539-2549 (1999).
Taupin, P., et al., "FGF-2-Responsive Neural Stem Cell Proliferation Requires CCg, a Novel Autocrine/Paracrine Cofactor," *Neuron* 28: 385-397 (2000).
Thomson, B.M., et al., "Preliminary Characterization of Porcine Bone Marrow Stromal Cells: Skeletogenic Potential, Colony-Forming Activity, and Response to Dexamethasone, Transforming Growth Factor β, and Basic Fibroblast Growth Factor," *J. Bone Min Res* 8(10): 1173-1183 (1993).
Woodbury, D., et al., "Adult Rat and Human Bone Marrow Stromal Cells Differentiate Into Neurons," *J. Neurosci. Res.* 61: 364-370 (2000).
Woodbury, D., et al., "Adult Rat and Human Bone Marrow Stromal Cells Differentiate into Neurons," *Society for Neuroscience* 26: Abstract 312.9 (2000).
Ross, J.A., et al., "Phenotypic Mapping of Human Mesothelial Cells," *Adv. Peritoneal Dialysis*, 14:25-30 (1998).
Cooper, L.F., et al., "Incipient Analysis of Mesenchymal Stem-cell-derived Osteogenesis," *J. Dent. Res.*, 80(1):314-320 (2001).
van den Bos, C., et al., "p21$^{cip1}$ Rescues Human Mesenchymal Stem Cells from Apoptosis Induced by Low-Density Culture," *Cell Tissue Res.*, 293:463-470 (1998).
Gartel, A.L., et.al., "Transcriptional Regulation of the p21$^{(WAF1/CIP1)}$ Gene," Exp. Cell Res., 246:280-289 (1999).
Ross, J.A., et al., "Phenotypic Mapping of Human Mesothelial Cells," Medline Abstract, Accession No. 200113945, Document No. 20113945, *Adv. Peritoneal Dialysis*, 14:25-30 (1998).
Batinic, D., et al., "Relationship Between Differing Volumes of Bone Marrow Aspirates and Their Cellular Composition," *Bone Marrow Transplantation*, 6:103-107 (1990).
Bruder, S.P., et al., "Growth Kinetics, Self-Renewal, and the Osteogenic Potential of Purified Human Mesenchymal Stem Cells During Extensive Subcultivation and Following Cryopreservation," *Journal of Cellular Biochemistry*, 64:278-294 (1997).
Caplan, A.I. and Bruder, Scott P., "Cell and Molecular Engineering of Bone Regeneration." In *Principles of Tissue Engineering*, R.P. Lanza et al., eds. (Texas: R.G. Lanes Company), Chapter 37: 603-618, (1997).
Lodie, T.A., et al., "Systematic Analysis of Reportedly Distinct Populations of Multipotent Bone Marrow-Derived Stem Cells Reveals a Lack of Distinction," *Tissue Engineering*, 8(5):739-751 (2002).
Müller-Ehmsen, Jochen, et al., "Rebuilding a Damaged Heart: Long-Term Survival of Transplanted Neonatal Rat Cardiomyocytes After Myocardial Infarction and Effect on Cardiac Function," *Circulation*, pp. 1720-1726 (2002).
Muschler, G.F., et al., "Aspiration to Obtain Osteoblast Progenitor Cells From Human Bone Marrow: The Influence of Aspiration Volume," *JBJA Journal of Bone and Joint Surgery-American*, 79A:1699-1709 (1997).
Pittenger, M.F., et al., Multilineage Potential of Adult Human Mesenchymal Stem Cells, Supplementary Material, http://www.Sciencemag.org/feature/data/983855.dt I (Apr. 2, 1999).

Quinones, R.R., "Hematopoietic Engraftment and Graft Failure After Bone Marrow Transplantation," *The American Journal of Pediatric Hematology/Oncology*, 15(1):3-17 (1993).
Van den Bos, C., et al., "Human Mesenchymal Stem Cells Respond to Fibroblast Growth Factors," *Human Cell*, 10(1):45-50 (1997).
Haynesworth, S.E., et al., "Cell Surface Antigens on Human Marrow-Derived Mesenchymal Cells are Detected by Monoclonal Antibodies," *Bone*, 13:69-80 (1992).
Reyes, M., et al., "Purification and ex vivo expansion of postnatal human marrow mesodermal progenitor cells," *Blood* 98:2615-2625, American Society of Hematology (Nov. 2001).
Wade, N., "Panel Finds Flawed Data in a Major Stem Cell Report," available online at http://www.nytimes.com/2007/02/28/science/28stem.html?ei=5070&en=b124e855015b1933&ex=117954, 2 pages, The New York Times Company (Feb. 2007).
Aldhous, P., and Reich, E.S., "Flawed stem cell data withdrawn," available online at http://www.newscientist.com/article.ns?id=mg19325915.200, 2 pages, New Scientist magazine (Feb. 2007).
Aldhous, P., and Reich, E.S., "Fresh questions on stem cell findings," available online at http://www.newscientist.com/article.ns?id=mg19325964.600, 3 pages, New Scientist magazine (Mar. 2007).
Check, E., "The hard copy," *Nature* 446:485-486, Nature Publishing Company (Mar. 2007).
Check, E., "Stem-cell paper corrected," *Nature* 447:763, Nature Publishing Company (Jun. 2007).
Chi, K.R., "Adult stem cell figure retracted," available online at http://www.the-scientist.com/news/home/53279/, 8 pages, The Scientist (Jun. 2007).
Freed, J., "Study on uses for adult stem cells was flawed, panel says," *Deseret Morning News*, available online at http://www.deseretnews.com/dn/print/1,1442,660198505,00.html, 2 pages, Deseret News Publishing Company (Feb. 2007).
Jiang, Y., et al., "Pluripotency of mesenchymal stem cells derived from adult marrow," *Nature* 418:41-49, Nature Publishing Company (Jul. 2002).
Jiang, Y., et al., "Corrigendum: Pluripotency of mesenchymal stem cells derived from adult marrow," *Nature* 447:879-880, Nature Publishing Company (Jun. 2007).
Jiang, Y. et al., "Multipotent progenitor cells can be isolated from postnatal murine bone marrow, muscle, and brain," *Exp. Hematol.* 30:896-904, Elsevier Science Inc. (Aug. 2002).
Jiang, Y., et al., "Errata: Multipotent progenitor cells can be isolated from urine bone marrow, and brain," *Exp. Hematol.* 30:896-904, Elsevier Science Inc. (Jun. 2006).
European Search Report dated Oct. 30, 2007.
Abu-Abeeleh, M., et al., "Efficacy of Human Adipose Tissue-derived Stem Cells in Cardiac Muscle Repair in an Experimental Acute myocardial Infarction Model Using nude Rats (Crl:NIH-Fox1$^{RNU}$)," *Comp. Clin. Pathol.* 19:593-600, Springer-Verlag London Limited, England (Nov. 2009).
Alberts, B., et al., eds., *Molecular Biology of the Cell*, Second Edition, p. 746, Garland Publishing Inc., United States (1989).
Al-Khaldi, A., et al., "Postnatal Bone Marrow Stromal Cells Elicit a Potent VEGF-Dependent Neoangiogenic Response In Vivo," *Gene Ther*.10:621-629, Nature Publishing Group, England (Apr. 2003).
Annex, B.H., "Therapeutic Angiogenesis: A Treatment for the New Millennium or Passing Fad?" *Cardiol. Rounds* 6:1-6, Snell Medical Communication Inc., United States (Jan. 2002).
Aprikyan, A.A., et al., "Erratum," *Exp. Hematol.* 34:1771-1772, Elsevier Inc., Netherlands (Dec. 2006).
Bao, P., et al., "The Role of Vascular Endothelial Growth Factor in Wound Healing," *J. Surg. Res.* 153:347-358, Academic Press, United States (May 2009).
Boodhwani, M. and Sellke, F.W., "Therapeutic Angiogenesis in Diabetes and Hypercholesterolemia: Influence of Oxidative Stress," *Antioxid. Redox Signal.* 11:1945-1959, Mary Ann Liebert, Inc., United States (Aug. 2009).
Brissova, M. and Powers, A.C., "Revascularization of Transplanted Islets—Can it Be Improved?" *Diabetes* 57:2269-2271, American Diabetes Association, United States (Sep. 2008).

(56) References Cited

OTHER PUBLICATIONS

Carmeliet, P., "Angiogenesis in Health and Disease," *Nat. Med.* 9:653-660, Nature Publishing Group, England (Jun. 2003).
Celis, J.E., ed. *Cell Biology: A Laboratory Handbook*, Second Edition, vol. 1, pp. 6-11, Academic Press, United States (1998).
Dai, W. and Kloner, R.A., "Experimental Cell Transplantation Therapy in Rat Myocardial Infarction Model Including Nude Rat Preparation," *Methods Mol. Biol.* 660: 99-109, Humana Press, New York City, United States (Aug. 2010).
Eskin, S.G., et al., "Human Smooth Muscle Cells Culture From Artherosclerotic Plaques and Uninvolved Vessel Wall," In Vitro 17:713-8, Tissue Culture Assn., United States (1981), abstract from NCBI PubMed, PMID No. 7327599.
Favia, G., et al., "Accelerated Wound Healing of Oral Soft Tissues and Angiogenic Effect Induced by a Pool of Amino Acids Combined to Sodium Hyaluronate NPL26 (AMINOGAM®)," *J Biol. Regul. Homeost. Agents* 22:109-116, BIOLIFE, s.a.s., Italy (Apr. 2008).
Frantz, S., et al., "Innate Immunity and Anggiogenesis," *Circ. Res.* 96:15-26, American Heart Association, Inc., United States (Jan. 2005).
Frödin, M. and Gammeltoft, S., "Insulin-like Growth Factors Act Synergistically with Basic Fibroblast Growth Factor and Nerve Growth Factor to Promote Chromaffin Cell Proliferation," *Proc. Natl. Acad Sci. U.S.A.* 91:1771-1775, National Academy of Sciences, United States (1994).
Gao, J., et al., "Tissue-Engineered Fabrication of an Osteochondral Composite Using Rat Bone Marrow-Derived Mesenchymal Stem Cells," *Tissue Eng.* 7:363-371, Mary Ann Liebert, Inc., United States (Aug. 2001).
Goldman, S. and Raya, T.E., "Rat Infarct Model of Myocardial Infarction and Heart Failure," *J. Card Fail.* 1:169-177, Churchill Livingstone, United States (1995).
Greenhalgh, D.G., et al., "Synergistic Actions of Platelet-derived Growth Factor and the Insulin-like Growth Factors in Vivo—Enhancement of Tissue Repair in Genetically Diabetic Mice," *Wound Repair Regen.* 1:69-81, Blackwell Science, United States (1993).
Hayflick, L. and Moorhead, P.S., "The Serial Cultivation of Human Diploid Cell Strains," *Exp. Cell Res.* 25:585-621, Academic Press, United States (1961).
Himes, B.T., et al., "Recovery of Function Following Grafting of Human Bone Marrow-derived Stromal Cells into the Injured Spinal Cord," *Neurorehabil. Neural Repair* 20:278-296, Sage Publications, United States (Jun. 2006), abstract from NCBI PubMed, PMID No. 16679505.
Jennemann, R., et al., "Specific Immunization Using Keyhole Limpet Hemocyanin-Ganglioside Conjugates," *J. Biochem.* 115:1047-1052, Oxford University Press, England (1994).
Ju, Y-J., et al., "Effects of Local Administration of Vascular Endothelial Growth Factor on Properties of the in Situ Frozen-Thawed Anterior Cruciate Ligament in Rabbits," *Am. J. Sports Med.* 34:84-91, Williams & Wilkins, United States (Jan. 2006).
Kaigler, D., et al., "Role of Vascular Endothelial Growth Factor in Bone Marrow Stromal Cell Modulation of Endothelial Cells," *Tissue Eng.* 9:95-103, Mary Ann Liebert, Inc., United States (Feb. 2003).
Lee, K.A., et al., "Increased Mesenchymal Cell Density Accompanies Induction of Tropoelastin Expression in Developing Elastic Tissue," *Dev. Dyn.* 200:53-67, Wiley-Liss, Inc., United States (1994).
Lee, K.D., et al., "In Vitro Hepatic Differentiation of Human Mesenchymal Stem Cells," *Hepatology* 40:1275-1284, Williams & Wilkins, United States (Dec. 2004).
Lewis, R.J., Sr., *Hawley's Condensed Chemical Dictionary*, Twelfth Edition, p. 28, Van Nostrand Reinhold, United States (1993).
Lu, B., et al., "Human Adult Bone Narrow-derived Somatic Cells Rescue Vision in a Rodent Model of Retinal Degeneration," *Exp. Eye Res.* 91:449-455, Academic Press, England (Jul. 2010).
Lynch, S.E., et al., "Growth Factors in Wound Healing—Single and Synergistic Effects on Partial Thickness Porcine Skin Wounds," *J. Clin. Invest.* 84:640-646, The American Society for Clinical Investigation, Inc., United States (1989).
Morris, W., ed., *The American Heritage Dictionary of the English Language*, New College Edition, pp. 353, Houghton Mifflin Company, United States (1976).
Murry, C.E., et al., "Haematopoietic Stem Cells Do Not Transdifferentiate Into Cardiac Myocytes in Myocardial Infarcts," *Nature* 428:664-668, Nature Publishing Group, England (Apr. 2004).
Okura, H., et al., "Cardiomyoblast-like Cells Differentiated from Human Adipose Tissue-Derived Mesenchymal Stem Cells Improve Left Ventricular Dysfunction and Survival in a RatMyocardial Infarction Model," *Tissue Eng. Part C Methods* 16:417-425, Mary Ann Liebert, Inc., United States (Jun. 2010).
Parnas, D. and Linial, M., "Culture Density Regulates Both the Cholinergic Phenotype and the Expression of the CNTF Receptor in P19 Neurons," *J Mol. Neurosci.* 8:115-130, Humana Press, United States (1997).
Peter, S.J., et al., "Marrow Stromal Osteoblast Function on a Poly(propylene Fumarate)/Beta-tricalcium Phosphate Biodegradable Orthopaedic Composite," *Biomaterials* 21:1207-1213, Elsevier Science, England (Jun. 2000), abstract from NCBI PubMed PMID No. 10811302.
Reinecke, H., et al., "Skeletal Muscle Stem Cells Do Not Transdifferentiate Into Cardiomyocytes After Cardiac Grafting," *J. Mol. Cell. Cardiol.* 34:241-249, Academic Press, England (Feb. 2002).
Reynolds, L.J., et al., "Density and Substrata are Important in Lung Type II Cell Transdifferentiation In Vitro," *Int. J Biochem. Cell Biol.* 31:951-960, Elsevier, Netherlands (1999).
Seidel, C.L., et al., "Effect of Seeding Density and Time in Culture on Vascular Smooth Muscle Cell Proteins," *Am. J. Physiol.* 254:C235-C242, American Physiological Society, United States (1988), abstract from NCBI PubMed, PMID No. 3279797.
Shirinsky, V.P., et al., "Density-Related Expression of Caldesmon and Vinculin in Cultured Rabbit Aortic Smooth Muscle Cells," *Exp. Cell. Res.* 194:186-189, Academic Press, United States (1991), abstract from NCBI PubMed, PMID No. 1902791.
SIGMA-ALDRICH, Inc., "Sigma-Aldrich Leukocyte Separation (Procedure No. 1119)," pp. 1, SIGMA-ALDRICH, Inc., United States (Sep. 2003).
Sun, Z., et al., "Human Angiogenic Cell Precursors Restore Function in the Infarcted Rat Heart: A Comparison of Cell Delivery Routes," *Eur. J. Heart Fail.* 10:525-533, Elsevier Science, Netherlands (Jun. 2008).
Unemori, E.N., et al., "Interleukin-1 and Transforming Growth Factor-α: Synergistic Stimulation of Metalloproteinases, PGE2, and Proliferation in Human Fibroblasts," *Exp. Cell Res.* 210:166-171, Academic Press, United States (1994).
Verfaillie, C. and Jiang, Y., "Errata," *Exp. Hematol.* 34:809, Elsevier Inc., Netherlands (Jun. 2006).
Volelkel, N.F., et al., "Angiogenesis in Chronic Lung Disease," *Chest* 131:874-879, American College of Chest Physicians, United States (Mar. 2007).
Voronov, E., et al., "IL-1 is Required for Tumor Invasiveness and Angiogenesis," *Proc. Natl. Acad. Sci. U.S.A.* 100:2645-2650, National Academy of Sciences, United States (Mar. 2003).
Xiong, Y., et al., "Neurorestorative Treatments for Traumatic Brain injury," *Discov. Med.* 10:434-442, Discovery Medicine, United States (Nov. 2010).
Xu, R., et al., "Serum Supplement, Inoculum Cell Density, and Accessory Cell Effects are Dependent on the Cytokine Combination Selected to Expand Human HPCs Ex Vivo," *Transfusion* 40:1299-1307, American Association of Blood Banks, United States (Nov. 2000), abstract from NCBI PubMed, PMID No. 11099656.
Yang, H., et al., "IL-1 Receptor Antagonist-Mediated Therapeutic Effect in Murine Myasthenia Gravis is Associated with Suppressed Serum Proinflammatory Cytokines, C3, and Anti-Acetylcholine Receptor Receptor IgG1," *J. Immunol.* 175:2018-2025, American Association of Immunologists, United States (Aug. 2005).
Yu, C., et al, "The Different Effects of TGF-β1, VEGF and PDGF on the Remodeling of the Anterior Cruciate Ligament Graft," in *Targets in Gene Therapy*, pp. 389-396, Y. You, ed., InTech, Croatia (Aug. 2011).

(56) References Cited

OTHER PUBLICATIONS

Zevin, S., et al., "Nicotine Transport in a human Choriocarcinoma Cell Line (JAR)," *J Pharm. Sci.* 87:702-706, American Pharmaceutical Assn., United States (1998), abstract from NCBI PubMed, PMID No. 9607946.
Amendment and Remarks in U.S. Appl. No. 11/084,256, dated Oct. 9, 2012.
Amendment and Response to Office Action in U.S. Appl. No. 11/268,234, dated Oct. 2, 2007.
Annotated Declaration of Armand Keating, M.D., FRCP(C) in Patent Interference No. 105,953, dated Feb. 18, 2014.
Communication in U.S. Appl. No. 11/238,234, dated Sep. 29, 2005.
Cross-Examination of Donald George Phinney, Ph.D. during Patent Interference No. 105,953, declared Jun. 25, 2013.
Curriculum Vitae of Armand Keating, M.D., dated Jul. 20, 2013.
Curriculum Vitae of Donald G. Phinney, Ph.D., in Patent Interference No. 105,953, dated Apr. 9, 2014.
Declaration of Armand Keating, M.D., FRCP(C) in Patent Interference No. 105,953, dated Feb. 18, 2014.
Declaration of Gene Kopen in U.S. Appl. No. 09/960,244, dated May 18, 2007.
Declaration of Robert J. Deans in U.S. Appl. No. 13/042,205 and U.S. Appl. No. 11/084,256, dated Mar. 25, 2013.
Declaration of Robert J. Deans, Ph.D. In Support of Request by Applicant for Interference in U.S. Appl. No. 10/048,757, dated Mar. 10, 2005.
Deposition of Gene C. Kopen, PhD in Patent Interference No. 105,953, dated Jan. 9, 2014.
Examination by Counsel for the Senior Party during Patent Interference No. 105,953, declared Jun. 26, 2013.
Examiner Interview Summary in U.S. Appl. No. 11/084,256, dated Feb. 22, 2013.
Non-Final Office Action in U.S. Appl. No. 09/960,244, dated Jul. 24, 2003.
Non-Final Office Action in U.S. Appl. No. 09/960,244, dated Mar. 7, 2007.
Non-Final Office Action in U.S. Appl. No. 09/960,244, dated Oct. 5, 2007.
Notice of Allowance in U.S. Appl. No. 09/960,244, dated Dec. 15, 2004.
Notice of Allowance in U.S. Appl. No. 09/960,244, dated Apr. 1, 2013.
Non-Final Office Action in U.S. Appl. No. 10/251,685, dated Mar. 7, 2007.
Non-Final Office Action in U.S. Appl. No. 10/251,685, dated Oct. 5, 2007.
Oral Deposition of Armand Keating, M.D. in Patent Interference No. 105,953, dated Mar. 20, 2014.
Preliminary Amendment and Request by Applicant for Interference in U.S. Appl. No. 10/048,757, dated Mar. 14, 2005.
Second Communication in U.S. Appl. No. 11/238,234, dated Dec. 24, 2008.
Second Declaration of Donald G. Phinney (For Lack of Enablement and Written Description and to Deny Benefit) in Patent Interference No. 105,953, dated Nov. 25, 2013.
Substitute First Declaration of Donald G. Phinney (For No Interference in Fact) in Patent Interference No. 105,953, dated Jan. 23, 2014.
Supplemental IDS in U.S. Appl. No. 11/238,234, dated Oct. 4, 2007.
U.S. Appl. No. 60/147,324, filed Aug. 6, 1999.
U.S. Appl. No. 60/164,650, filed Nov. 10, 1999.
"Monitoring Stem Cell Research: A Report of the President's Council on Bioethics", Washington, D.C. Jan. 2004.
"Mouse Anti-Human Cd49c Monoclonal Antibody, FITC", Creative BioMart. 2013. Accessed Nov. 16, 2013. http://www.creativebiomart.net/description_67446_27.htm.
"Statement from the University of Minnesota: University Misconduct Panel Concludes that Certain Data in Stem Cell Paper Were Falsified." Accessed Dec. 15, 2017. http://www.stmedia.startribune.com/documents/U+of+MN+Investigation+Statement.doc.

Adelman et al., "Multilineage embryonic hematopoiesis requires hypoxic ARNT activity", Genes & Development 13:2478-2483 (1999).
Alberts et al., Molecular Biology of the Cell Second Edition, 746. New York: Garland Publishing, Inc., 1989.
Alberts et al., Molecular Biology of the Cell Third Edition, 1187-1189. New York: Garland Publishing, Inc., 1994.
Aldhous et al., "Flawed stem cell data withdrawn", New Scientist Feb. 17-23, 2007; 193(2591):12.
Aldhous et al., "Fresh questions on stem cell findings", New Scientist Mar. 24-30, 2007; 193(2596):12-13.
Aldhous et al., "Further doubts of stem-cell images", New Scientist Aug. 8-14, 2009; 203(2720):12.
Baddoo et al., "Characterization of Mesenchymal Stem Cells Isolated From Murine Bone Marrow by Negative Selection", Journal of Cellular Biochemistry 89:1235-1249 (2003).
Baker, "Flawed data in multipotent cell study", Nature Reports Stem Cells, published online Jun. 21, 2007. doi:10.1038/stemcells.2007.40.
Blair et al., "Lack of Expression of Thy-1 (CD90) on Acute Myeloid Leukemia Cells With Long-Term Proliferative Ability In Vitro and In Vivo", Blood 89(9):3104-3112 (1997).
Bradley et al., "The Effect of Oxygen Tension on Haemopoietic and Fibroblast Cell Proliferation In Vitro", Journal of Cellular Physiology 97:517-522 (1978).
Brewer, "Isolation and culture of adult rat hippocampal neurons", Journal of Neuroscience Methods 71:143-155 (1997).
Breyer et al., "Multipotent adult progenitor cell isolation and culture procedures", Experimental Hematology 34:1596-1601 (2006).
Caplan, "The Mesengenic Process", Bone Repair and Regeneration 21(3):429-435 (1994).
Chakravarthy et al., "Culture in low levels of oxygen enhances in vitro proliferation potential of satellite cells from old skeletal muscles", Cellular and Molecular Life Sciences 58:1150-1158 (2001).
Chan et al., "Enhanced Plating Efficiency of Trypsin-Adapted Human Embryonic Stem Cells is Reversible and Independent of Trisomy 12/17", Cloning and Stem Cells 10(1):107-117 (2008).
Check, "Stern Cells: The Hard Copy", Nature 446:485-486 (2007).
Cipolleschi et al., "The expansion of murine bone marrow cells preincubated in hypoxia as an in vitro indicator of their marrow-repopulating ability", Leukemia 14:735-739 (2000).
Cipolleschi et al., "The Role of Hypoxia in the Maintenance of Hematopoietic Stem Cells", Blood 82(7):2031-2037 (1993).
Colter et al., "Rapid expansion of recycling stem cells in cultures of plastic-adherent cells from human bone marrow", PNAS 97(7):3213-3218 (2000).
Conget et al., "Phenotypical and Functional Properties of Human Bone Marrow Mesenchymal Progenitor Cells", Journal of Cellular Physiology 181:6773 (1999).
Csete et al., "Oxygen-Mediated Regulation of Skeletal Muscle Satellite Cell Proliferation and Adipogenesis in Culture", Journal of Cellular Physiology 189:189-196 (2001).
Dayan et al., "Human mesenchymal stromal cells improve scar thickness without enhancing cardiac function in a chronic ischaemic heart failure model", Interactive CardioVascular and Thoracic Surgery 14:516-520 (2012).
Deans et al., "Mesenchymal stem cells: Biology and potential clinical uses", Experimental Hematology 28:875-884 (2000).
Digirolamo et al., "Propagation and senescence of human marrow stromal cells in culture: a simple colony-forming assay identifies samples with the greatest potential to propagate and differentiate", British Journal of Haematology 107:275-281 (1999).
Eckfeldt et al., "The Molecular Repertoire of the 'Almighty' Stem Cell", Nature Reviews Molecular Cell Biology 6:727-736 (2005).
Friedenstein et al., "Osteogenesis in transplants of bone marrow cells", Journal of Embryology and Experimental Morphology 16(3):381-390 (1966).
Friedenstein et al., "The Development of Fibroblast Colonies in Monolayer Cultures of Guinea-Pig Bone Marrow and Spleen Cells", Cell and Tissue Kinetics 3:393-403 (1970).

(56) References Cited

OTHER PUBLICATIONS

Glimm et al., "Human hematopoietic stem cells stimulated to proliferate in vitro lose engraftment potential during their S/G2/M transit and do not reenter G0", Blood 96(13):4185-4193 (2000).
Gospodarowicz et al., "Growth Factors in Mammalian Cell Culture", Annual Reviews of Biochemistry 45:531-559 (1976).
Gothot et al., "Cell Cycle-Related Changes in Repopulating Capacity of Human Mobilized Peripheral Blood CD34+ Cells in Non-Obese Diabetic/Severe Combined Immune-Deficient Mice", Blood 92:2641-2649 (1998).
Gstraunthaler, "Alternatives to the Use of Fetal Bovine Serum: Serum-free Cell Culture", ALTEX 20(4):275-281 (2003).
Gupta et al., "Effect of Oxygen on the Clonal Growth of Adherent Cells (CFU-F) from Different Compartments of Mouse Bone Marrow", Experimental Hematology 15:1153-1157 (1987).
Held et al., "The Effect of Oxygen Tension on Colony Formation and Cell Proliferation of Amniotic Fluid Cells In Vitro", Prenatal Diagnosis 4:171-179 (1984).
Hyun, "The bioethics of stem cell research and therapy", The Journal of Clinical Investigation 120:71-75 (2010).
Ivanovi et al., "Primitive human HPCs are better maintained and expanded in vitro at 1 percent oxygen than 20 percent", Transfusion 40:1482-1488 (2000).
Ivanovic et al., "Incubation of murine bone marrow cells in hypoxia ensures the maintenance of marrow-repopulating ability together with the expansion of committed progenitors", British Journal of Haematology 108:424-429 (2000).
Jacobs et al., "Immunological characteristics of human mesenchymal stem cells and multipotent adult progenitor cells", Immunology and Cell Biology 91:32-39 (2013).
Januszevvicz et al., "Requirements for Growth of Human Erythroid Progenitors in Nutrient Agar", American Journal of Hematology 15:207-217 (1983).
Jiang et al., "Multipotent progenitor cells can be isolated from postnatal murine bone marrow, muscle, and brain", Experimental Hematology 30:896-904 (2002).
Jiang et al., "Pluripotency of mesenchymal stem cells derived from adult marrow", Nature 418:41-49 (2002).
Katahira et al., "Improvement of Culture Conditions for Human Megakaryocytic and Pluripotent Progenitor Cells by Low Oxygen Tension", International Journal of Cell Cloning 5:412-420 (1987).
Kiel et al., "SLAM Family Receptors Distinguish Hematopoietic Stem and Progenitor Cells and Reveal Endothelial Niches for Stem Cells", Cell 121:11091121 (2005).
Kisselbach et al., "CD90 Expression on human primary cells and elimination of contaminationg fibroblasts from cell cultures", Cytotechnology 59:31-44 (2009).
Koller et al., "Beneficial Effects of Reduced Oxygen Tension and Perfusion in Long-Term Hematopoietic Cultures", Annals of the New York Academy of Sciences 665:105-106 (1992).
Koller et al., "Effects of Synergistic Cytokine Combinations, Low Oxygen, and Irradiated Stroma on the Expansion of Human Cord Blood Progenitors", Blood 80(2):403-411 (1992).
Kopen et al., "Marrow stromal cells migrate throughout forebrain and cerebellum, and they differentiate into astrocytes after injection into neonatal mouse brains", PNAS 96:10711-10716 (1999).
Lakshmipathy et al., "Stem cell plasticity", Blood Reviews 19:29-38 (2005).
Lazarus et al., "Ex vivo expansion and subsequent infusion of human bone marrow-derived stromal progenitor cells (mesenchymal progenitor cells): implications for therapeutic use", Bone Marrow Transplantation 16:557-564 (1995).
Lennon et al., "Cultivation of Rat Marrow-Derived Mesenchymal Stem Cells in Reduced Oxygen Tension: Effects on In Vitro and In Vivo Osteochondrogenesis", Journal of Cellular Physiology 187:345-355 (2001).
Lo Nigro et al., "Expression and Function of Pluripotency Genes in Adult Stem Cells", In Adult Stem Cells: Biology and Methods of Analysis, Stem Cell Biology and Regenerative Medicine, edited by D. G. Phinney, 95-112. New York: Humana Press, 2011.

Maeda et al., "Enhanced Colony Formation of Human Hemopoietic Stem Cells in Reduced Oxygen Tension", Experimental Hematology 14:930-934 (1986).
Nash et al., "New T Cell—Activation Inhibitors for Prevention of Acute Graft-Versus-Host Disease", Blood and Marrow Transplantation Reviews 10(2):1-20 (2001).
Nash et al., "The Response of Cultured Human Retinal Pigment Epithelium to Hypoxia: A Comparison to Other Cell types", Investigative Ophthalmology & Visual Science 35(6):2850-2856 (1994).
Oguro et al., "SLAM Family Markers Resolve Functionally Distinct Subpopulations of Hematopoietic Stem Cells and Multipotent Progenitors", Cell Stem Cell 13:102-116 (2013).
Okamoto et al., "Clonal heterogeneity in differentiation potential of immortalized human mesenchymal stem cells", Biochemical and Biophysical Research Communications 295:354-361 (2002).
Phinney, "Building a Consensus Regarding the Nature and Origin of Mesenchymal Stem Cells", Journal of Cellular Biochemistry Supplement 38:7-12 (2002).
Phinney et al., "Donor Variation in the Growth Properties and Osteogenic Potential of Human Marrow Stromal Cells", Journal of Cellular Biochemistry 75:424-436 (1999).
Pittenger et al., "Mesenchymal Stem Cells", In Human Cell Culture vol. V Primary Mesenchymal Cells, edited by M.R. Koller et al., vii, 198-206. New York: Kluwer Academic Publishers, 2001.
Pittenger et al., "Multilineage Potential of Adult Human Mesenchymal Stem Cells", Science 284:143-147 (1999).
Prockop et al., "Biotechnology of Extracellular Matrix", Biochemical Society Transactions 28(4):341-345 (2000).
Prockop et al., "Potential use of marrow stromal cells as therapeutic vectors for diseases of the central nervous system", Progress in Brain Research 128:293-297 (2000).
Quinlan et al., "Effect of Hypoxia on the Hematopoietic and Immune Modulator Preprotachykinin-l", Archives of Surgery 133:1328-1334 (1998).
Reyes et al., "Purification and ex vivo expansion of postnatal human marrow mesodermal progenitor cells", Blood 98(9):2615-2625 (2001).
Reyes et al., "Purification and ex vivo expansion of postnatal human marrow mesodermal progenitor cells", Blood 98:2615-2625 (2001).
Reykdal et al., "Effect of nitric oxide production and oxygen tension on progenitor preservation in ex vivo culture", Experimental Hematology 27:441450 (1999).
Robertson, "Human embryonic stem cell research: ethical and legal issues", Nature Genetics 2:74-78 (2001).
Rossant, "Stem Cells from the Mammalian Blastocyst", Stem Cells 19:477-482 (2001).
Schooley et al., "Growth of Murine Bone Marrow Adherent Stromal Cells in Culture Without Hydrocortisone in a Low Oxygen Environment", International Journal of Cell Cloning 3:2-9 (1985).
Sekiya et al., "Expansion of Human Adult Stem Cells from Bone Marrow Stroma: Conditions that Maximize the Yields of Early Progenitors and Evaluate Their Quality", Stem Cells 20:530-541 (2002).
Serafini et al., "Hematopoietic reconstitution by multipotent adult progenitor cells: precursors to long-term hematopoietic stem cells", The Journal of Experimental Medicine 204(1):1296-139 (2007).
Shimaoka et al., "Nurse-like Cells from Bone Marrow and Synovium of Patients with Rheumatoid Arthritis Promote Survival and Enhance Function of Human B Cells", Journal of Clinical Investigation 102(3):606-618 (1998).
Suh et al., "Cell transformation by the superoxide-generating oxidase Mox1", Nature 401:79-82 (1999).
Thomson et al., "Embryonic Stem Cell Lines Derived from Human Blastocysts", Science 282:1145-1147 (1998).
Tolar et al., "Hitting the right spot with mesenchymal stromal cells (MSCs)", Stem Cells 28(8):1446-1455 (2010).
Tomita et al., "Improved heart function with myogenesis and angiogenesis after autologous porcine bone marrow stromal cell transplantation", The Journal of Thoracic and Cardiovascular Surgery 123:1132-1140 (2002).
Travlos, "Normal Structure, Function, and Histology of the Bone Marrow", Toxicologic Pathology 34(5):548-565 (2006).

(56) References Cited

OTHER PUBLICATIONS

Tremain et al., "MicroSAGE Analysis of 2,353 Expressed Genes in a Single Cell-Derived Colony of Undifferentiated Human Mesenchymal Stem Cells Reveals mRNAs of Multiple Cell Lineages", Stern Cells 19:408-418 (2001).
Trombi et al., "Selective Culture of Mesodermal Progenitor Cells", Stem Cells and Development 18(8):1227-1234 (2009).
Ulloa-Montoya et al., "Culture Systems for Pluripotent Stem Cells", Journal of Bioscience and Bioengineering 100(1):12-27 (2005).
Urao et al., "Redox regulation of stem/progenitor cells and bone marrow niche", Free Radical Biology and Medicine 54:26-39 (2013).
Verfaillie, "Adult stem cells: assessing the case for pluripotency", Trends in Cell Biology 12(11):502-508 (2002).
Verfaillie et al., "Stem Cells: Hype and Reality", Hematology 2002(1):369- 391 (2002).
Viswanathan et al., "Soliciting Strategies for Developing Cell-Based Reference Materials to Advance MSC Research and Clinical Translation", Stem Cells and Development 23(11):1157-1167 (2014).
Walia et al., "Enrichment for Breast Cancer Cells with Stem/Progenitor Properties by Differential Adhesion", Stem Cells and Development 19(8):1175-1182 (2010).

* cited by examiner

CELL POPULATIONS WHICH CO-EXPRESS CD49C AND CD90

BACKGROUND OF THE INVENTION

A number of conditions and diseases of the central nervous system (i.e., brain and spinal cord), peripheral nervous system and heart adversely affect humans. These conditions and diseases include, for example, spinal cord injury, amyotrophic lateral sclerosis (ALS), Parkinson's disease, stroke, traumatic brain injury, brain tumors, Fabry Disease, congestive heart failure and myocardial infarction. Clinical management strategies, for example, frequently focus on the prevention of further damage or injury rather than replacement or repair of the damaged tissue (e.g., neurons, glial cells, cardiac muscle); include treatment with exogenous steroids and synthetic, non-cellular pharmaceutical drugs; and have varying degrees of success which may depend on the continued administration of the steroid or synthetic drug.

For example, the majority of spinal cord injuries are compression injuries with the remaining cases involving complete transection of the spinal cord. Current therapeutic treatments for spinal cord injury include the prevention of additional spinal cord injury by physically stabilizing the spine through surgical and non-surgical procedures and by inhibiting the inflammatory response with steroidal therapy. Thus, there is a need to develop new, improved and effective methods of treatment for diseases and conditions, in particular, neurological and cardiac diseases and conditions, in humans.

SUMMARY OF THE INVENTION

The present invention relates to cell populations which co-express CD49c and CD90 and methods of treating conditions, such as neurological or cardiac conditions, in humans with these populations of cells.

In one embodiment, the invention is a substantially homogenous cell population which co-expresses CD49c, CD90 and telomerase.

In another embodiment, the invention is a substantially homogenous cell population which co-expresses CD49c and CD90, but does not express bone sialoprotein (BSP).

In yet another embodiment, the invention is a substantially homogenous cell population which co-expresses CD49c and CD90, wherein the cell population does not express CD34 and/or CD45.

In a further embodiment, the invention is a substantially homogenous cell population which co-express CD49c, CD90 and at least one trophic factor selected from the group consisting of BDNF, IL-6, NGF and MCP-1.

In still another embodiment, the invention includes a method of making a substantially homogenous cell population which co-express CD49c and CD90 by culturing a source of the cell population a seeding cell density of less than about 100 cells/cm$^2$ under a low oxidative stress condition and selecting from the cultured source of the cell population, cells which co-express CD49c and CD90.

In a further embodiment, the invention includes a method of making a substantially homogenous cell population which co-express CD49c and CD90 by culturing a source of the cell population at a seeding density of less than about 100 cells/cm$^2$ under a low oxidative stress condition; and selecting from the cultured source of the cell population, cells which co-express CD49c and CD90.

In another embodiment, the invention is a method of making a substantially homogenous cell population which co-express CD49c and CD90 by culturing a source of the cell population at a seeding density of less than about 50 cells/cm$^2$ under a low oxidative stress condition; and selecting from the cultured source of the cell population, cells which co-express CD49c and CD90.

In still another embodiment, the invention is a method of making a substantially homogenous cell population which co-express CD49c and CD90 by culturing a source of the cell population at a seeding density of less than about 30 cells/cm$^2$ under a low oxidative stress condition; and selecting from the cultured source of the cell population, cells which co-express CD49c and CD90.

A further embodiment of the invention is a method of making a substantially homogenous cell population which co-express CD49c and CD90 by culturing a source of the cell population at a seeding density of less than about 75,000 cells/cm$^2$ under a low oxidative stress condition to produce an adherent cell population and culturing the adherent cell population at a seeding density of less than about 100 cells/cm$^2$ under a low oxidative stress condition. Cells which co-express CD49c and CD90 are selected from the cultured adherent cell population.

Another embodiment of the invention includes a method of making a substantially homogenous cell population which co-express CD49c and CD90 by culturing a source of the cell population at a seeding cell density of less than about 50 cells/cm$^2$ under a low oxygen condition and selecting from the cultured source of the cell population, cells which co-express CD49c and CD90.

In yet another embodiment, the invention includes a method of making a substantially homogenous cell population which co-express CD49c and CD90 by culturing a source of the cell population at a seeding cell density of less than about 30 cells/cm$^2$ under a low oxygen condition and selecting from the cultured source of the cell population, cells which co-express CD49c and CD90.

In a further embodiment, the invention is a method of making a substantially homogenous cell population which co-express CD49c and CD90 by culturing a source of the cell population at a seeding cell density of less than about 75,000 cells/cm$^2$ under a low oxygen condition to produce an adherent cell population; culturing the adherent cell population at an initial density of less than about 100 cells/cm$^2$ under a low oxygen condition; and selecting from the cultured adherent cell population, cells which co-express CD49c and CD90.

Another embodiment of the invention is a method of treating a human suffering from a degenerative or acute injury condition, comprising the step of administering to the human a substantially homogenous cell population which co-express CD49c and CD90.

In yet another embodiment, the invention includes a method of treating a human suffering from a neurological condition, comprising the step of administering to the human a substantially homogenous cell population which co-express CD49c and CD90.

In still another embodiment, the invention is a method of treating a human suffering from a cardiac condition to the human a substantially homogenous cell population which co-express CD49c and CD90.

An additional embodiment of the invention is a method of treating a human suffering from a neurological condition by culturing a source of a cell population at a seeding cell density of less than about 100 cells/cm$^2$ under a low oxygen condition; selecting from the cultured source of the cell population, a population of cells which co-express CD49c and CD90; and administering the population of cells which co-express CD49c and CD90 to the human.

In yet an additional embodiment, the invention includes a method of treating a human suffering from a neurological condition, comprising culturing a source of a cell population; selecting from the cultured source of the cell population, a population of cells which co-express CD49c and CD90; and administering the population of cells which co-express CD49c and CD90 to the human.

In still another embodiment, the invention is a method of making a committed progenitor cell, comprising culturing a source of a cell population; selecting from the cultured source of the cell population, cells which co-express CD49c and CD90; and modifying the cells which co-express CD49c and CD90 to become committed progenitor cells.

An additional embodiment of the invention includes a method of treating a human suffering from a neurological condition, comprising culturing a source of a cell population; selecting from the cultured source of the cell population, cells which co-express CD49c and CD90; modifying the cells which co-express CD49c and CD90 to become a committed progenitor cell; and administering the modified cells to the human.

In another embodiment, the invention relates to a method of treating a human suffering from a degenerative or acute injury condition by administering to the human a substantially homogenous cell population which co-express CD49c, CD90 and telomerase.

In another embodiment, the invention provides a pharmaceutical composition comprising a substantially homogenous cell population which co-express CD49c and CD90.

In yet another embodiment, the invention provides a pharmaceutical composition comprising a substantially homogenous cell population which co-express CD49c, CD90 and telomerase.

A further embodiment of the invention is a method of treating a human suffering from a neurological condition, comprising the step of administering to the human a substantially homogenous cell population which co-express CD49c, CD90 and telomerase.

In another embodiment, the invention is a method of treating a human suffering from a degenerative or acute injury condition, comprising the step of administering to the human a substantially homogenous cell population which co-express CD49c and CD90, but does not express bone sialoprotein (BSP).

In yet another embodiment, the invention is a method of treating a human suffering from a neurological condition, comprising the step of administering to the human a substantially homogenous cell population which co-express CD49c and CD90, but does not express bone sialoprotein.

In still another embodiment, the invention is a substantially homogenous cell population which co-expresses CD49c, CD90 and at least one cardiac-related transcription factor.

An additional embodiment of the invention is a substantially homogenous cell population which co-expresses CD49c, CD90, and at least one cardiac-related transcription factor, but does not express bone sialoprotein.

In a further embodiment, the invention is a substantially homogenous cell population which co-expresses CD49c, CD90, GATA4, Irx4 and Nkx2.5.

In yet another embodiment, the invention is a substantially homogenous cell population which co-expresses CD49c, CD90, telomerase, GATA4, Irx4 and Nkx2.5.

In additional embodiment, the invention is a method of making a substantially homogenous cell population which co-expresses CD49c, CD90 and at least one cardiac-related transcription factor, comprising the steps of culturing a source of the cell population under a low oxygen condition and treating the cultured source of the cell population with a protein kinase C inhibitor and a DNA methylation inhibitor.

In still another embodiment, the invention is a method of making a substantially homogenous cell population which co-expresses CD49c, CD90, telomerase and at least one cardiac-related transcription factor, comprising the steps of culturing a source of the cell population under a low oxygen condition and treating the cultured source of the cell population with the protein kinase C inhibitor and a DNA methylation inhibitor.

Another embodiment of the invention includes a method of making a substantially homogenous cell population which co-expresses CD49c, CD90, telomerase, GATA4, Irx4, Nkx2.5, comprising the steps of culturing a source of the cell population under a low oxygen condition and treating the cultured source of the cell population with a protein kinase C inhibitor and a DNA methylase inhibitor.

In a further embodiment, the invention includes a method of making a substantially homogenous cell population which co-expresses CD49c, CD90, GATA4, Irx4, Nkx2.5, comprising the steps of culturing a source of the cell population under a low oxygen condition and treating the cultured source of the cell population with a protein kinase C inhibitor and a DNA methylation inhibitor.

An additional embodiment of the invention includes a method of making a substantially homogenous cell population which co-expresses CD49c, CD90 and at least one cardiac-related transcription factor, comprising the step of treating a cell population which co-expresses CD49c and CD90 with a protein kinase C inhibitor and a DNA methylation inhibitor.

In still another embodiment, the invention is a method of making a substantially homogenous cell population which co-expresses CD49c, CD90, telomerase and at least one cardiac-related transcription factor, comprising the step of treating a cell population which co-expresses CD49c, CD90 and telomerase with a protein kinase C inhibitor and a DNA methylation inhibitor.

Another embodiment of the invention is a method of making a substantially homogenous cell population which co-expresses CD49c, CD90, telomerase, GATA4, Irx4 and Nkx2.5, comprising the step of treating a cell population which co-expresses CD49c, CD90 and telomerase with a protein kinase C inhibitor and a DNA methylation inhibitor.

In yet another embodiment, the invention provides a method of treating a myocardial infarction or a congestive heart failure in a human, comprising the step of administering a substantially homogenous cell population which co-expresses CD49c, CD90 and at least one cardiac-related transcription factor to the human.

A further embodiment of the invention is a method of treating a myocardial infarction or a congestive heart failure in a human, comprising the step of administering a substantially homogenous cell population which co-expresses CD49c, CD90, telomerase and at least one cardiac-related transcription factor to the human.

In yet another embodiment, the invention provides a method of treating a myocardial infarction or a congestive heart failure in a human, comprising the step of administering a substantially homogenous cell population which co-expresses CD49c, CD90, GATA4, Irx4 and Nkx2.5 to the human.

In another embodiment, the invention is a method of treating a myocardial infarction or a congestive heart failure in a human, comprising the step of administering a substantially homogenous cell population which co-expresses CD49c, CD90, telomerase, GATA4, Irx4, Nkx2.5 to the human.

In a further embodiment, the invention is a method of treating a myocardial infarction or a congestive heart failure in an individual, comprising the steps of culturing a source of a cell population under a low oxygen condition; treating the cultured source of the cell population with a protein kinase C inhibitor and a DNA methylation inhibitor; and administering the treated cell population to the individual.

Another embodiment of the invention includes a method of treating a myocardial infarction or congestive heart failure in a human, comprising the steps of treating a cell population which co-expresses CD49c and CD90 with a protein kinase C inhibitor and a DNA methylation inhibitor; and administering the treated cells to the human.

An additional embodiment of the invention includes a method of forming a committed progenitor cell-type, comprising the step of combining a substantially homogenous population of cells that co-expresses CD49c and CD90 with a population of cells that includes at least one committed progenitor cell type.

Another embodiment of the invention is a substantially homogenous cell population which co-expresses CD49c, CD90 and has a doubling time of less that about 144 hours when cultured under a low oxygen condition.

A further embodiment of the invention is a substantially homogenous cell population which co-expresses CD49c, CD90 and has a doubling time less than about 144 hours when cultured under a low oxygen condition, wherein the substantially homogenous cell population is formed by a method, comprising the step of culturing a source of the cell population at a seeding density of about 100 cells/cm$^2$ under the low oxygen condition.

In still another embodiment, the invention includes a pharmaceutical composition comprising a substantially homogenous cell population which co-expresses CD49c, CD90 and at least one cardiac-related transcription factor.

In yet an additional embodiment, the invention includes a pharmaceutical composition comprising a substantially homogenous cell population which co-expresses CD49c, CD90, telomerase and at least one cardiac-related transcription factor.

In still another embodiment, the invention includes a pharmaceutical composition comprising a substantially homogenous cell population which co-expresses CD49c, CD90, telomerase, GATA4, Irx4, and Nkx2.5.

Another embodiment of the invention is a pharmaceutical composition comprising a substantially homogenous cell population which co-expresses CD49c, CD90, GATA4, Irx4 and Nkx2.5.

The invention described herein provides a substantially homogenous population of cells for treating a condition or disease in a human. Advantages of the cell based therapies of the claimed invention include, for example, incorporation of the cells into the tissue (e.g., central nervous system tissue, peripheral nervous system tissue, cardiac tissue); the incorporated cells have the potential to differentiate or develop into neuronal, glial or other cells (e.g., cardiac muscle) to replace or facilitate repair of the damaged, traumatized or degenerating tissue thereby resulting in a more permanent treatment of the degenerative, acute injury, traumatized, neurological or cardiac condition; and the ability to employ characterized reproducible populations of cells in treatment regimens. The cells of the invention have the potential to secret beneficial cytokines and trophic factors (e.g., BDNF, IL-6, NGF and MCP-1).

Thus, treatment of humans with populations of cells which co-express CD49c and CD90 can potentially reverse, diminish or repair the loss due to a degenerative, acute injury, neurological (e.g., Parkinsons disease, ALS, stroke, traumatic brain injury, brain tumors) or cardiac condition (e.g., congestive heart failure, myocardial infarction) in a human, thereby increasing the quality of life and life expectancy for the human.

DETAILED DESCRIPTION OF THE INVENTION

Figure 1A:
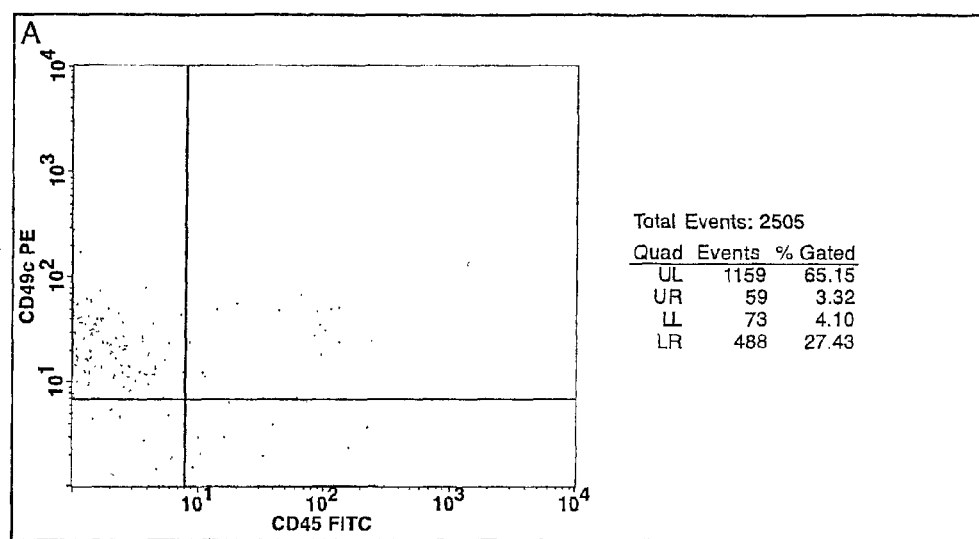
FIGS. 1A, 1B, and 1C illustrate the flow cytometric analysis of cell populations in the Primary (1A) and Master (1B and 1C) Cell Banks generated from a bone marrow aspirate following red blood cell lysis.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The teachings of application Ser. No. 09/960,244, filed Sep. 21, 2001, entitled "Cell Populations Which Co-Express CD49c and CD90," are incorporated by reference in their entirety.

The present invention relates to a substantially homogeneous cell population of cells which co-express CD49c and CD90. The invention also relates to a substantially homogeneous cell population of cells which co-express CD49c, CD90 and telomerase. The invention further relates to a substantially homogeneous cell population of cells which co-express CD49c and CD90, but does not express bone sialoprotein (BSP). The invention also relates to a substantially homogenous cell population of cells which co-express CD49c, CD90 and at least one cardiac-related transcription factor (e.g., GATA4, Irx4 and Nkx2.5). The invention additionally relates to a substantially homogenous cell population which co-expresses CD49c, CD90, telomerase and at least one cardiac-related transcription factor.

"Substantially homogenous" as used herein refers to a population of cells wherein the majority (e.g., between about 100% to about 70%; between about 100% to about 90%) of the total number of cells have a specified characteristic of interest (e.g., co-express CD49c and CD90; co-express CD49c, CD90 and telomerase; co-express of CD49c and CD90 with minimal expression of CD34 and/or CD45).

In one embodiment, the substantially homogenous population of cells which co-express CD49c and CD90 is a population of cells wherein between about 80% to about 90% of the cells co-express the cell surface antigens CD49c and CD90. In another embodiment, the substantially homogenous population of cells is a population of cells wherein between about 70% to about 80% of the cells co-express the cell surface antigens CD49c and CD90. In a further embodiment, the substantially homogeneous population of cells is a population of cells, wherein at least a portion of individual cells expresses CD49c, CD90 and telomerase. In one embodiment, a majority of individual cells each co-expresses CD49c, CD90 and telomerase.

"Co-express" or "co-expresses," as used herein, refers to the simultaneous detection of two or more molecules, e.g., CD49c and CD90; CD49c, CD90 and telomerase; CD49c, CD90, GATA4, Nkx2.5 and Irx4; CD49c, CD90, telomerase, GATA4, Nkx2.5 and Irx4, on or in a single cell; or, alternatively, on or in a collection of cells.

The substantially homogenous cell population of the invention co-express CD49c, CD90 and telomerase on a single cell of the population; or CD49c and CD90 on a single cell of the population. The cell population of the invention which co-expresses CD49c, CD90 and, optionally, telomerase on each cell of the population, can also co-express other proteins (e.g., cardiac-related transcription factors such as GATA4, Irx4 and Nkx2.5) on at least a portion (e.g., about 10%, about 20%, about 50%, about 70%, about 80%, about 90%) of the total number of cells in the cell population.

Techniques to detect co-expression of CD49c and CD90 in cells (e.g., bone marrow stromal cells) are well established. For example, co-expression of CD49c and CD90 on a cell can be detected by multiple color cytometric analysis. CD49c can be detected employing a fluorescein labeled probe and CD90 can be detected employing a Texas red probe. The CD49c and CD90 cell surface antigens can be visualized with the aid of a flow cytometer equipped with multiple filters capable of detecting the multiple colors. Techniques to detect the molecules of interest can also include ELISA, RIA, immunofluorescence microscopy and quantitative PCR.

In another embodiment, the invention is a substantially homogenous cell population of the invention which co-express CD49c and CD90, but does not express bone sialoprotein.

The substantially homogenous cell population of the invention which co-express CD49c and CD90 and, optionally, telomerase, has a doubling time less than between about 144 hours to about 48 hours. In one embodiment, the doubling time of the cell population is less than about 144 hours. In another embodiment, the doubling time of the cell population is less than about 72 hours. In yet another embodiment, the doubling time of the cell population is less than about 65 hours. In still another embodiment, the doubling time is less than about 48 hours. In an additional embodiment, the doubling time is less than about 35 hours. In a further embodiment, the doubling time is less than about 30 hours. The doubling time of the cells of the invention can be varied depending on, for example, the density of the cells in culture (e.g., 100 cells/cm$^2$) and/or the concentration of oxygen employed to culture the cells (e.g., a low oxygen concentration such as about 5% oxygen).

The substantially homogenous cell population which co-express CD49c and CD90 can have the potential to differentiate into a preselected phenotype (e.g., chondrocytes, astrocytes, oligodendrocytes, neurons, bone, osteoclasts, osteoblasts, cardiomyocytes, pancreatic islet cells, skeletal muscle, smooth muscle, hepatocytes and retinal ganglial cells). The potential to differentiate into a preselected phenotype refers to the ability of the cell population to change to a functional cell type.

The substantially homogenous cell population which co-express CD49c and CD90 do not, after between about 20 population doublings to about 50 population doublings, substantially express at least one cell senescent marker selected from a group consisting of P21 and P53. A senescent marker would be any marker associated with senescence or aging in a cell (e.g., P21, P53). The senescent marker can be a cytoplasmic, nuclear or cell surface marker.

In one embodiment, the cells of the invention undergo about 20 population doublings and still co-express CD49c and CD90 but do not substantially express at least one cell senescent marker selected from a group consisting of P21 and P53. In another embodiment, the cells of the invention undergo about 30 population doubling and still co-express CD49c and CD90 but do not substantially express at least one cell senescent marker selected from a group consisting of P21 and P53. In yet another embodiment, the cells of the invention undergo about 40 population doublings and still co-express CD49c and CD90 but do not substantially express at least one cell senescent marker selected from a group consisting of P21 and P53. In still another embodiment, the cells of the invention undergo about 50 population doublings and still co-express CD49c and CD90 but do not substantially express at least one cell senescent marker selected from a group consisting of P21 and P53. One of skill in the art would be able to determine when a cell has undergone a population doubling (Freshney, R. I. "Culture of Animal Cells: A Manual of Basic Techniques" New York, Wiley-Liss (1994)) and be able to determine whether the cell populations co-express CD49c and CD90 and do not substantially express at least one cell senescent marker selected from a group consisting of P21 and P53 employing established techniques (e.g., flow cytometry, quantitative PCR).

The substantially homogenous cell population of the invention which co-express CD49c and CD90 can further include expression of P21 or P53 after between about 20 to about 50 population doublings of the cells. Expression of a senescent marker (e.g., P21, P53) is a relative expression of the senescent marker (e.g., relative to 18s rRNA GAPDH (Glyceraldehyde-3-phosphate dehydrogenase), actin). "Relative expression," as used herein, is expression (e.g., nucleic acid, protein) of a molecule of interest (e.g., CD49c, CD90, telomerase, CBFA1, BSP, BDNF, IL-6, MCP-1) with respect to expression of a standard or reference marker (e.g. 18s rRNA, actin, GFAP). In a preferred embodiment, expression of P53 is a relative expression of up to about 3000 transcripts of P53 (e.g., 0, 100, 1000, 1500, 2000) per $10^6$ transcripts of an 18s rRNA and expression of P21 is a relative expression of up to about 20,000 transcripts of P21 per $10^6$ transcripts of an 18s rRNA.

In one embodiment, the expression of p53 is about 3000 transcripts of p53 per $10^6$ transcripts of an 18s rRNA. In another embodiment, the expression of p53 is about 2000 transcripts of p53 per $10^6$ transcripts of an 18s rRNA. In yet another embodiment, the expression of p53 is about 1000 transcripts of p53 per $10^6$ transcripts of an 18s rRNA.

In another embodiment, the expression of p21 is up to about 20,000 transcripts of p21 (e.g., 0, 100, 1000, 5000, 10000, 15000, 20000) per $10^6$ transcripts of an 18s rRNA. In still another embodiment, the expression of p21 is about 15,000 transcripts of p21 per $10^6$ transcripts of an 18s rRNA. In yet another embodiment, the expression of p21 is about 500 transcripts of p21 per $10^6$ transcripts of an 18s rRNA.

In one embodiment, the expression of a bone lineage marker core binding factor 1 (CBFA1) (Otto, F. et al., Cell 89(5) 765-771 (1997)) is about 5000 transcripts of the bone lineage marker per $10^6$ transcripts of an 18s rRNA. In another embodiment, the expression of the bone lineage marker CBFA1 is about 3000 transcripts of the bone lineage marker per $10^6$ transcripts of an 18s rRNA. In still another embodiment, the expression of the bone lineage marker CBFA1 is about 1000 transcripts of the bone lineage marker per $10^6$ transcripts of an 18s rRNA.

The substantially homogenous cell population of the invention can be a cell population from any human tissue (e.g., bone marrow, fat, skin, placenta, muscle, umbilical cord blood). In a preferred embodiment, the substantially homogeneous cell population is derived from bone marrow cells (e.g., human bone marrow stromal cells). Cells of the invention can be referred to as "derived" from any human tissue. Cells derived from tissues can be obtained, for example, by lysis of the source of the cells (e.g., bone marrow cells). For example, bone marrow stromal cells are derived from whole bone marrow aspirates after ammonium chloride lysis of the bone marrow aspirates. The ammonium chloride removes red blood cells from the aspirates and the resulting cell pellet is employed to generate the substantially homogenous cell population which co-express CD49c and CD90 cells of the invention. Alternatively, the bone marrow can be processed (e.g., fractionated by density gradient centrifugation, $NH_2Cl$ lysis, fluorescent activated sorting or magnetic sorting) to derive the cell populations of the invention. For example, the bone marrow aspirates or lysed bone marrow cells are passed through a density gradient to separate the cells of the invention from cellular debris as a result of lysis. Alternatively, or additionally, the bone marrow aspirates or lysed bone marrow cells can form a density gradient.

Whole bone marrow aspirates are obtained from a human and cultured in contact with a solid phase. Alternatively, or additionally, the whole bone marrow aspirate can be processed to yield a mononuclear cell fraction which is then cultured in contact with a solid phase. The solid phase can be, for example, plastic (e.g., tissue culture treated plastics).

The mononuclear cell fraction can be obtained from a whole bone marrow aspirate on a density gradient by established procedures. Alternatively, the mononuclear cell fraction is obtained by lysis of the red blood cells contained in the bone marrow aspirate. The lysis is done by mixing the bone marrow aspirate with ammonium chloride.

Human bone marrow cells are obtained from healthy human donors by aspirations of the iliac crest and bone marrow stromal cell populations obtained employing well-established techniques. For example, substantially homogenous cell populations which co-express CD49c and CD90 are obtained from human iliac crest bone marrow aspirates and processed to mononuclear cell fractions from which bone marrow stromal cells are selectively propagated in vitro based upon their propensity to attach to plastic and divide in response to defined cell culture medium. The plastic-adherent cells are optimally grown at a cell concentration that encourages virtually only the self-renewing cells, referred to as colony-forming unit fibroblast-like cells (Cfu-f), to proliferate. The Cfu-f-derived cells are analyzed for cells which co-express CD49c and CD90 and sub-cultured to produce a substantially homogenous cell population which co-express CD49c and CD90.

The bone marrow aspirate, or a cellular fraction of the bone marrow aspirate, is cultured in contact with a solid phase and an intermediate cell population is isolated from the resulting cell culture based on their propensity to adhere to the solid phase. Bone marrow aspirates, or a cellular fraction of the aspirate, are cultured at a dissolved oxygen concentration of less than about 20%, preferably between about 1% to about 10%, and most preferably from between about 2% oxygen to about 7% oxygen. In a preferred embodiment, the dissolved oxygen concentration is about 5% oxygen. The resulting adherent cell population is expanded to yield a substantially homogeneous cell population which co-express CD49c and CD90.

Bone marrow cell expansion is conducted with a seeding density of less than about 2500 cell/cm$^2$, preferably less than about 1000 cells/cm², and most preferably less than about 100 cells/cm². In a particular embodiment, the initial cell density in the expansion step is between about 30 cells/cm² to about 50 cells/cm². A seeding density would be the number of adherent cells per cm² obtained from mononuclear bone marrow cells.

Standard media preparations can be used to culture the bone marrow cells. For example, the media can be minimum essential medium-alpha modification supplemented with 4 mM L-glutamine and 0 to 10% lot selected fetal bovine serum (FSB), preferably about 10% FSB. The culturing step can be conducted for any reasonable period, for example, between about 3 to about 25 days and most preferably between about 3 to about 15 days.

An intermediate cell population is isolated from the cell culture describe above based on its propensity to adhere to the solid phase. The intermediate cell population is grown at a cell concentration that encourages virtually only the self-renewing cells, referred to herein as colony-forming unit fibroblast-like cells (Cfu-f), to proliferate. The Cfu-f-derived cells are sub-cultured under defined conditions to produce a substantially homogeneous population of cells (Example 1). According to the invention, the expansion yields a substantially homogeneous cell population which co-express CD 49 and CD 90.

In another embodiment, the substantially homogenous cell population does not express CD34 and/or CD45. The presence or absence of CD34 and CD45 can be detected on bone marrow mononuclear cells which co-express CD49c and CD90 using routine methods including, for example, antigen-specific ELISA assays, quantitative PCR, or flow cytometry. Cells which co-express CD49c and CD90, but do not express either or both CD34 and/or CD45, are propagated in culture and stored until use in the methods of the invention.

In yet another embodiment, the substantially homogenous population of cells co-expressing CD49c and CD90 express a trophic factor selected from the group consisting of brain-derived neurotrophic factor (BDNF) (Barde, Y. A., et al. *EMBO J.*, 1(5):549-553 (1982)), nerve growth factor (NGF) (Levi-Montalcini, R., Arch Biol 76(2):387-417 (1965)), neurotrophin-3 (NT-3) (Mohn, A., et al., *Nature* 344:339-341 (1990)), interleukin-6 (IL-6) (Barton, B. E., *Clin. Immumol. Immunopathol.* 85(1):16-20 (1997)), interleukin-7 (IL-7), interleukin-11 (IL-11), stem cell factor (SCF), macrophage chemoattractant protein-1 (MCP-1), matrix metalloproteinase-9 (MMP-9) and Cystatin-C and vascular endothelial growth factor (VEGF) (Moore, M A., et al., *Ann. N.Y. Acad. Sci.*, 938:36-45 (2001); Kollermann, J., et al., *Am. J. Clin. Pathol.* 116:115-121 (2002)).

Expression of BDNF, NGF, NT-3, IL-6, IL-7, IL-11, SCF, VEGF, MCP-1, MMP-9 and Cystatin-C in substantially homogenous populations of cells co-expressing CD49c and CD90 can be augmented by a variety of techniques, including ex vivo cultivation of the cells in chemically defined medium.

In yet another embodiment, the invention is a substantially homogenous cell population which co-express CD49c, CD90 and telomerase. Expression of telomerase is a relative expression, for example, a relative expression of greater than between about 1 transcript of telomerase per $10^6$ transcripts of an 18s rRNA and about 10 transcripts of telomerase per $10^6$ transcripts of an 18s rRNA. In one embodiment, expression of telomerase is about 1 transcript of telomerase per $10^6$ transcripts of an 18s rRNA. In another embodiment, expression of telomerase is about 5 transcripts of telomerase per $10^6$ transcripts of an 18s rRNA. In yet another embodiment, expression of telomerase is about 10 transcripts of telomerase per $10^6$ transcripts of an 18s rRNA.

The cell population which co-expresses CD49c, CD90 and telomerase has a doubling time of less than about 144 hours, less than about 72 hours or less than about 48 hours.

The cell population which co-expresses CD49c, CD90 and telomerase has the potential to differentiate into a preselected phenotypes (e.g., a chondrocyte, an astrocyte, an oligodendrocyte, a neuron, osteocyte, osteoblast, osteoclast, a cardiomyocyte, a pancreatic islet cell, a skeletal muscle, a smooth muscle, a hepatocyte and a retinal ganglial cell).

The cell population which co-expresses CD49c, CD90 and telomerase can further include expression of P21 or P53 after between about 20 to about 50 population doublings of the cells (e.g., 20, 30, 40 or 50 population doublings). Expression of P53 is a relative expression of up to about 3000 transcripts of P53 per $10^6$ transcripts of an 18s rRNA (e.g., 3000, 2000 or 1000 transcripts of P53 per $10^6$ transcripts of an 18s rRNA). Expression of P21 is a relative expression of up to about 20,000 transcripts of P21 per $10^6$ transcripts of an 18s rRNA (e.g., 20000, 15000 or 5000 transcripts of P21 per $10^6$ transcripts of an 18s rRNA).

In another embodiment, the cell population which co-expresses CD49c, CD90 and telomerase does not express CD34 and/or CD45. In yet another embodiment, the cell population which co-expresses CD49c, CD90 and telomerase express at least one trophic factor selected from the group consisting of BDNF, IL-6 and MCP-1.

In still another embodiment, the invention includes a method of making a substantially homogenous cell population which co-expresses CD49c and CD90 comprising culturing a source of the cell population (e.g., human bone marrow cells) and selecting from the cultured source of the cell population, cells which co-express CD49c and CD90. In one embodiment, the source of the cell population is cultured under a low oxygen condition (e.g., less than atmospheric). "Low oxygen condition," as used herein, refers to a concentration (e.g., percent of oxygen based on volume, weight or molarity) which is less than atmospheric oxygen.

In still another embodiment, the invention includes a method of making a substantially homogenous cell population which co-express CD49c, CD90 and telomerase comprising culturing a source of the cell population (e.g., human bone marrow cells) and selecting from the cultured source of the cell population, cells which co-express CD49c, CD90 and telomerase.

In a further embodiment, the invention includes a method of making a substantially homogenous cell population which co-express CD49c and CD90 but does not express bone salioprotein comprising culturing a source of the cell population and selecting from the cultured source of the cell population, cells which co-express CD49c, CD90 and a bone lineage marker.

In one embodiment, the concentration of oxygen ($O_2$) is less than about 21 mole percent (volume). In another embodiment, the concentration of oxygen ($O_2$) is less than about 23% by weight. In a preferred embodiment, the low oxygen condition is an oxygen concentration less than about 15% by volume (mole percent) oxygen, and more preferably an oxygen concentration less than about 10% by volume, and most preferably an oxygen concentration is less than about 5% by volume oxygen. In another embodiment, the source of the cell population is cultured at a seeding density of less than about 100 cells/cm² (e.g., 95, 90, 80, 50, 30, 25 cells/cm²) under low oxygen conditions (e.g., less than atmospheric, less than about 5% oxygen).

In an additional embodiment, the invention includes a method of making a substantially homogenous cell population which co-express CD49c and CD90 comprising culturing a source of the cell population (e.g., human bone marrow cells) and selecting from the cultured source of the cell population, cells which co-express CD49c and CD90 by culturing the source of the cell population under low oxidative stress (e.g., glutathione, Vitamin C, Catalase, Vitamin E, N-Acetylacysteine). "Low oxidative stress," as used herein, refers to conditions of no or minimal free radical damage to the cultured cells.

The method of making a substantially homogenous population of cells which co-express CD49c and CD90; co-express CD49c, CD90 and telomerase; or co-express CD49c, CD90 but does not express bone salioprotein (BSP), can further include lysing the source of the cell population (e.g., bone marrow aspirates) prior to culturing the source of the cell population. For example, lysis of a bone marrow aspirate can result in the lysis of hematopoietic cells leaving the non-hematopoietic cells un-lysed. Additionally, or alternatively, the method can further include fractionating (e.g., by passage through or formation of a density gradient, by NH$_2$Cl lysis) the source of the cell population (e.g., bone marrow aspirates) prior to culturing the source of the cell population.

The cells made by the method of the invention can also express at least one trophic factor (e.g., BDNF, NGF, NT-3, IL-6, IL-7, IL-11, SCF, MCP-1, MMP-9, Cystatin-C and VEGF). In another embodiment, the substantially homogenous population of cells which co-express CD49c and CD90; co-express CD49c, CD90 and telomerase; co-express CD49c, CD90 but does not express bone salioprotein, made by the method of the invention do not express CD34 and/or CD45.

In still another embodiment, the invention is a method of treating a human suffering from a degenerative or acute injury condition, comprising the step of administering to the human a substantially homogenous cell population which co-expresses CD49c and CD90. The cells used to treat the human suffering from a degenerative or acute injury condition can also not express CD34 and/or CD45.

Degenerative disease is a disease in which the decline (e.g., function, structure, biochemistry) of particular cell type (e.g., neuronal, muscle, connective, epithelial) results in an adverse clinical condition. For example, Parkinson's disease is a degenerative disease in the central nervous system (e.g., basal ganglia) which is characterized by rhythmical muscular tremors, rigidity of movement, festination, droopy posture and masklike facies. Degenerative diseases that can be treated with the substantially homogenous cell populations of the invention which co-express CD49c and CD90 can be, for example, Parkinson's disease, Huntington's disease, Alzheimer's disease, amyotrophic lateral sclerosis, congenital heart failure, cardiomyopathy, ataxias, and spinal muscular dystrophy.

An acute injury condition is a condition in which an event or multiple events results in an adverse clinical condition. The event which results in the acute injury condition can be an external event such as blunt force or compression or an internal event such as sudden ischemia (e.g., stroke or heart attack). Acute injury conditions that can be treated with the substantially homogenous cell populations of the invention which co-express CD49c and CD90; which co-express CD49c, CD90 and telomerase; which co-express CD49c and CD90, but does not express bone sialoprotein (BSP), can be, for example, spinal cord injury, traumatic brain injury, myocardial infarction, congestive heart failure and stroke.

In a further embodiment, the invention includes a method of treating a human suffering from a cardiac condition, comprising the step of administering to the human a substantially homogenous cell population which co-express CD49c and CD90. A cardiac condition is a disease of the heart. The disease of the heart can be a disease of the cardiac muscle, connective tissue of vessels of the heart. The cells used to treat the human suffering from a cardiac condition can also not express CD34 and/or CD45. A cardiac condition that can be treated by the cells of the invention can be, for example, myocardial infarction, congestive heart failure, myocarditis, vascular heart disease, cardiomyopathy, congenital heart disease, ischemic heart disease, heart transplant and pre-transplantation bridge.

An additional embodiment of the invention includes a method of treating a human suffering from a neurological condition, comprising the step of administering to the human a substantially homogenous cell population which co-express CD49c and CD90; co-express CD49c, CD90 and telomerase; CD49c, CD90 and a bone lineage marker. "A neurological condition," as used herein, refers to any state of the nervous system (central or peripheral nervous system) which deviates in any manner from a normal nervous system or nervous system of a mammal (e.g., human) not affected by a neurological condition. The neurological condition can be a condition of the central (brain or spinal cord) or peripheral nervous system. The neurological condition can be, for example, the result or consequence of a disease (e.g., amyotrophic lateral sclerosis, Parkinson's Disease, Fabry Disease), acute injury condition (e.g., stroke, brain injury, spinal cord injury) or a combination of disease and acute injury condition. Other neurological conditions which can be treated with the substantially homogenous population of cells of the invention which co-express CD49c and CD90 include, for example, metachromatic dystrophy, adrenal leukodystrophy, Canavan disease, Pelizaeus Merzbacher disease, Nieman-Pick disease and a brain tumor.

In still another embodiment, the invention includes a method of treating a human suffering from a neurological condition, comprising culturing (e.g., low oxygen conditions; oxygen conditions less than atmospheric; about 5% oxygen) a source of a cell population (e.g., bone marrow, fat, cord blood, skin) and selecting from the cultured source of the cell population, a population of cells which co-express CD49c and CD90. The selected population of cells which co-express CD49c and CD90 are administered to the human.

In one embodiment, the substantially homogenous population of cells which are administered to the human co-express CD49c and CD90 and lack CD34 and/or CD45. In another embodiment, the substantially homogenous population of cells which are administered to the human co-express CD49c, CD90 and telomerase. In yet another embodiment, the substantially homogenous population of cells which are administered to the human co-express CD49c and CD90 or co-express CD49c, CD90 and telomerase and express at least three trophic factors selected from the group consisting of BDNF, NGF, NT-3, IL-6, IL-7, IL-11, SCF, MCP-1, MMP-9 and Cystatin-C (e.g., BDNF, IL-6 and MCP-1).

The synthesis and secretion of cytokines and trophic factors from the substantially homogenous population of cells of the invention can protect surrounding cells near or distant from the site of transplantation from further damage as a consequence of the degenerative, acute injury or neurological condition. The synthesis and secretion of cytokines and trophic factors from the substantially homogenous population of cells of the invention can also, or alternatively, promote regeneration of cells and tissues of the host (e.g., human suffering from a acute injury, neurological, cardiac or degenerative condition) treated with the substantially homogenous population cells of the invention which co-express CD49c and CD90 or co-express CD49c, CD90 and telomerase.

The substantially homogenous population of cells which co-express CD49c and CD90 or which co-express CD49c, CD90 and telomerase when administered to the human may respond to cellular signaling and physiological cues in the human and migrate to the area of injury or trauma and, therefore, be used as delivery vehicles for proteins and genes of interest.

In another embodiment, the invention is a method of treating a human suffering from a neurological condition (e.g., spinal cord injury, an amyotrophic lateral sclerosis, a Parkinson's Disease, a stroke, a traumatic brain injury, a Fabry Disease condition, metachromatic dystrophy, adrenal leukodystrophy, Canavan disease, Pelizaeus Merzbacher disease, Nieman-Pick disease, a brain tumor) by culturing a source of a cell population at a seeding density of less than about 100 cells/cm$^2$ under a low oxygen condition; selecting from the cultured source of the cell population, a population of cells which co-express CD49c and CD90; and administering the population of cells which co-express CD49c and CD90 to the human.

The transplantation of the substantially homogenous cell populations of the invention into a patient suffering from a neurological condition may result in the differentiation of the cells of the invention into cells which normally function in the nervous tissue affected in the human with the neurological condition thereby treating a myriad of neurological conditions including, for example, Parkinson's disease, ALS, spinal cord injury, brain tumors, stroke. Similarly, the homogenous cell populations of the invention can be used to treat a human suffering from a non-neurological condition such as a burn, heart disease, diabetes, osteoarthritis and rheumatoid arthritis. In a particular embodiment, the substantially homogenous cell populations of the invention administered to a patient (also referred to herein as an individual, in a particular human) suffering from a cardiac condition (e.g., myocardial infarction) can differentiate into cardiac muscle cells (also referred to herein as cardiomyocytes).

The cell populations of the invention may have the capacity to respond to intrinsic signals (e.g., at the sites of transplantation or when incorporated into tissues and organs) and exogenous cues to differentiate into numerous cell types (e.g., neuronal, glial, astrocytes, oligodendrocytes) in the human. The cell populations of the invention can provide a readily available source of cells for use in treating humans. The cell populations of the invention can be readily isolated from adult or embryonic tissues, proliferate at high rates, have large expansion potential, can be stable for long periods of time, can be responsive to exogenous signals and can produce sufficient therapeutic quantities of molecules of interest.

Accordingly, another embodiment of the invention is a method of making a committed progenitor cell by culturing (e.g., under a low oxygen condition, 5% oxygen) a source of a cell population (e.g., bone marrow cells, human bone marrow cells, fat, cord blood, skin) and selecting from the cultured source of the cell population cells which co-express CD49c and CD90. The population of cells which co-express CD49c and CD90 are modified to become committed progenitor cells. The selection of cells from the cultured source of the cell population cells which co-express CD49c and CD90 is achieved by a low oxygen condition (e.g., oxygen below atmospheric oxygen, 5% oxygen).

"Committed progenitor cell," as used herein, refers to a precursor cell obtained from a source (e.g., human bone marrow, fat, cord blood, skin) which develops into a cell for a particular purpose. A committed progenitor cell can be, for example, a CD49c/CD90 cell derived from human bone marrow which can differentiate or develop into, for example, a neuron, glial, astrocyte, oligodendrocyte cell or cardiac muscle cell.

In another embodiment, the invention is a method of treating a human suffering from a neurological condition by culturing a source of a cell population (e.g., bone marrow aspirates) and selecting (e.g., by a low oxygen culture condition) from the cultured source of the cell population, cells which co-express CD49c and CD90; co-express CD49c, CD90 and telomerase; or co-express CD49c, CD90 and a bone lineage marker. The selected cells which co-express, for example, CD49c and CD90 are modified to become a committed progenitor cell and administered to a human with a neurological condition (e.g., a spinal cord injury, an amyotrophic lateral sclerosis, a Parkinson's Disease, a stroke, a traumatic brain injury, a Fabry Disease condition, metachromatic dystrophy, adrenal leukodystrophy, Canavan disease, Pelizaeus Merzbacher disease, Nieman-Pick disease and a brain tumor).

Techniques to assess whether a cell of the substantially homogenous population of cells of the invention which co-express CD49c and CD90; co-express CD49c, CD90 and telomerase; or CD49c, CD90 but does not express bone salioprotein (BSP) become committed progenitor cells are within the expertise of one of skill in the art. For example, cells which co-express CD49c and CD90 can be cultured, selected and modified to produce and express the neuronal cell markers, such as noggin, musashi or Sox2, which would indicate that the cells are committed neuronal progenitors cells. Techniques to determine whether a cell has become a committed progenitor cell are well-established and known to one of skill in the art (e.g., quantitative PCR, flow cytometry).

Cells which co-express CD49c and CD90 can be selected from a source of a cell population for making the committed progenitor cells. Selected cells which co-express CD49c and CD90 (also referred to herein as "selected cells") can be, for example, modified to become committed progenitor cells by culturing the selected cells in:

1. DMEM/F12/ITS/2 mM Glutamine/BSA1 mg/ml;
2. DMEM/F12/ITS/2 mM Glutamine/BSA1 mg/ml/0.25 ng/ml IL-β;
3. DMEM/F12/ITS/2 mM Glutamine/BSA 1mg/ml/2 ng/ml TNFα;
4. DMEM/F12/ITS/2 mM Glutamine/BSA1 mg/ml/100 ng/ml NT-3;
5. DMEM/F12/ITS/2 mM Glutamine/BSA1 mg/ml/100 ng/ml Noggin;
6. DMEM/F12/ITS/2 mM Glutamine/BSA1 mg/ml/100 ng/ml GDNF;
7. DMEM/F12/ITS/2 mM Glutamine/BSA1 mg/ml/20 ng/ml/bFGF;
8. DMEM/F12/ITS/2 mM Glutamine/BSA1 mg/ml/10 μM Forskolin;
9. DMEM/F12/ITS/2 mM Glutamine/BSA1 mg/ml/1 μM Bay K 8644; and/or
10. DMEM/F12/B27/2 mM Glutamine/BSA1 mg/ml.
11. MEM-Alpha/4 mM Glutamine/10% ser lot selected fetal bovine serum and 5 mM nifedipine Selected cells can be used directly from cultures or stored for future use (e.g., by freezing in liquid nitrogen).

In one embodiment, the committed progenitor cells of the invention do not express CD34 and/or CD45. In another embodiment, the committed progenitor cells of the invention express at least one trophic factor selected from the group consisting of BDNF, NGF, NT-3, IL-6, IL-7, IL-11, SCF, MCP-1, VEGF, matrix metalloproteinase-9 (MMP-9) and Cystatin-C (e.g., BDNF, IL-6 and MCP-1).

In an additional embodiment, the invention is a method of treating a human suffering from a neurological condition, comprising culturing a source of a cell population (e.g., bone marrow, human bone marrow, fat, cord blood, skin) and selecting from the cultured source of the cell population cells which co-express CD49c and CD90. The selected cells are modified to become a committed progenitor cell. The committed progenitor cells are administered to a human.

In another embodiment, the invention is a substantially homogenous cell population which co-expresses CD49c, CD90 and at least one cardiac-related transcription factor. The cell population which co-expresses CD49c, CD90 and at least one cardiac-related transcription factor can further include expression of telomerase. In a preferred embodiment, the substantially homogenous cell population which co-expresses CD49c, CD90 and at least one cardiac-related transcription factor are derived from human bone marrow cells.

"Cardiac-related transcription factor," as used herein, refers to a protein, or the gene encoding a protein, or portion of a protein, which regulates the transcription of genes associated with or expressed by cardiac muscle cells. In a particular embodiment, the cardiac-related transcription factor is selected from the group consisting of GATA-binding transcription factor 4 (GATA4) (Auda-Boucher, G. et al., *Dev. Bio.* 225:214-225 (2000)); Iroquois Homeobox Gene 4 (Irx4) (Bao, Z., et al., *Science* 283:1161-1164 (1999); Auda-Boucher, G., et al., *Dev. Bio.* 225:214-225 (2000)); and Nkx2.5/CSX (Cardio specific Homeobox), also referred to as "Nkx2.5," (Bao, Z., et al., *Science* 283:1161-1164 (1999); Auda-Boucher, G., et al., *Dev. Bio.* 225:214-225 (2000)).

The substantially homogenous cell population which co-expresses CD49c, CD90, at least one cardiac-related transcription factor, and, optionally, telomerase, can differentiate into a cardiac muscle cell (also referred to herein as a cardiomyocyte). The substantially homogenous cell population which co-expresses CD49c, CD90, at least one cardiac-related transcription factor, and, optionally, telomerase, can also express at least one trophic factor (e.g., IL-6, VEGF, MCP1, BDNF).

In another embodiment, the invention provides a substantially homogenous cell population in which co-expresses CD49c, CD90 and at least one cardiac-related transcription factor, but does not express bone sialoprotein. The substantially homogenous cell population, which does not express bone sialoprotein, can also express a cardiac-related transcription factor (e.g., GATA4, Irx4, Nkx2.5).

In an additional embodiment, the invention provides a substantially homogenous cell population which co-expresses CD49c, CD90, and at least one member selected from the group consisting of GATA4, Irx4 and Nkx2.5. This substantially homogenous cell population can further express telomerase.

In still another embodiment, the invention is a method of making a substantially homogenous cell population which co-expresses CD49c, CD90 and at least one cardiac-related transcription factor comprising culturing a source of the cell population under a low oxygen condition and treating the cultured source of the cell population with the protein kinase C inhibitor (e.g., chelerythrine, H-7 dehydrochloride, K252a, staurosporine, bisindolylmaleimide I-V and Calphostin C) and a DNA methylation inhibitor (e.g., azacytidine). The method can further include selecting from the treated cell population cells which co-express CD49c, CD90 and at least one cardiac-related transcription factor.

In a preferred embodiment, the source of the cell population used in the methods of the invention includes a bone marrow source. In a more preferred embodiment, the bone marrow source is an adult bone marrow source.

In a particular embodiment, the protein kinase C inhibitor used in the methods of the invention is chelerythrine and the DNA methylation inhibitor is 5-azacytidine.

In a further embodiment, the invention is a method of making a substantially homogenous cell population which co-expresses CD49c, CD90, telomerase and at least one cardiac-related transcription factor comprising the steps of culturing a source of the cell population under a low oxygen condition and treating the cultured source of the cell population with a protein kinase C inhibitor and a DNA methylation inhibitor.

The substantially homogenous cell populations of the invention which co-express CD49c, CD90 and at least one cardiac-related transcription factor have longer doubling times (e.g., less than about 72 hours, less than about 65 hours, less than about 60 hours) than cells of the invention which were not treated with a protein kinase C inhibitor and a DNA methylation inhibitor and do not express at least one cardiac-related transcription factor. The cell populations of the invention can be labeled. Labeled cells can be administered to individuals (e.g., laboratory animals, such as rats, mice, or humans) and the fate of the labeled cells determined at a time (e.g., days, months, years) after administration. The cells can be radiolabeled, fluorescently labeled, or labeled with other compounds (e.g., biotin) to permit localization in the individual.

In yet another embodiment, the invention includes a method of making a substantially homogenous cell population which co-expresses CD49c, CD90, telomerase and at least one cardiac-related transcription factor, comprising the steps of culturing a source of the cell population (e.g., adult bone marrow cells) under a low oxygen condition and treating the cultured source of the cell population with a protein kinase C inhibitor (e.g., chelerythrine) and a DNA methylation inhibitor (e.g., 5-azacytidine).

In still another embodiment, the invention is a method of making a substantially homogenous cell population which co-expresses CD49c, CD90, telomerase, GATA4, Irx4 and Nkx2.5, comprising the steps of culturing a source of a cell population under a low oxygen condition and treating the cultured source of the cell population with a protein kinase C inhibitor and a DNA methylation inhibitor. The method further includes selecting from the treated cell population, cells which co-express CD49c, CD90, telomerase, and at least one member selected from the group consisting of GATA4, Irx4 and Nkx2.5.

In an additional embodiment, the invention is the method of making a substantially homogenous cell population which co-expresses CD49c, CD90, GATA4, Irx4, and Nkx2.5, comprising the steps of culturing a source of a cell population under low oxygen conditions and treating the cultured source of the cell population with a protein kinase C inhibitor in a DNA methylation inhibitor. Cells which co-express CD49c, CD90, telomerase, GATA4, Irx4 and Nkx2.5 can be selected from the treated cells.

An additional embodiment of the invention includes a method of making a substantially homogenous cell population which co-expresses CD49c, CD90 and at least one cardiac-related transcription factor, comprising the step of treating a cell population which co-expresses CD49c and CD90 with a protein kinase C inhibitor and a DNA methylation inhibitor.

In still another embodiment, the invention is a method of making a substantially homogenous cell population which co-expresses CD49c, CD90, telomerase and at least one cardiac-related transcription factor, comprising the step of treating a cell population which co-expresses CD49c, CD90 and telomerase with a protein kinase C inhibitor and a DNA methylation inhibitor.

Another embodiment of the invention is a method of making a substantially homogenous cell population which co-expresses CD49c, CD90, telomerase, GATA4, Irx4 and Nkx2.5, comprising the step of treating a cell population which co-expresses CD49c, CD90 and telomerase with a protein kinase C inhibitor and a DNA methylation inhibitor.

The methods of the invention can further include selecting from the treated cells, cells which co-express CD49c, CD90 and at least one cardiac-related transcription factor (e.g., GATA4, Irx4, Nkx2.5); and cells which co-express CD49c, CD90, telomerase and at least one cardiac-related transcription factor.

In one embodiment, the cell population of the invention can be a stem cell population. In another embodiment, the cell population of the invention can be an isolated cell population or an isolated stem cell population.

Cell populations of the invention, in particular, cell populations which co-express at least one cardiac-related transcription factor, can be used to treat a cardiac condition such as a myocardial infarction or congestive heart failure in a human. In one embodiment, the invention includes a method of treating a myocardial infarction or congestive heart failure in an individual (e.g., a human), comprising the step of administering a substantially homogenous cell population which co-expresses CD49c, CD90, at least one cardiac-related transcription factor and, optionally, telomerase, to the individual.

In a particular embodiment, the cardiac-related transcription factor expressed by the cells used to treat the myocardial infarction in the human is selected from the group consisting of GATA4, Irx4 and Nkx2.5 (also referred to herein as "Nkx2.5/CSX").

In a preferred embodiment, the cell populations of the invention are administered proximate to the location of the cardiac condition (e.g., myocardial infarction, congestive heart failure). For example, in a human suffering from a myocardial infarction, the cell populations of the invention are administered proximate to the myocardial infarction (e.g., into the cardiac muscle at the site of the infarct). The cells of the invention can be administered directly into the cardiac muscle tissue or spaces of the heart (the ventricular or atrial spaces).

In still another embodiment, the invention includes a method of treating a myocardial infarction or a congestive heart failure in a human comprising the steps of culturing a source of a cell population (e.g., adult bone marrow cells) under a low oxygen condition; treating the cultured source of the cell population with a protein kinase C inhibitor (e.g., chelerythrine) and a DNA methylation inhibitor (e.g., 5-azacytidine); and administering the treated cell population to the human.

In yet another embodiment, the invention includes a method of treating a myocardial infarction or a congestive heart failure in a human, comprising the steps of treating the cell population (e.g., adult bone marrow cells) which co-express CD49c and CD90 with a protein kinase C inhibitor (e.g., chelerythrine) and a DNA methylation inhibitor (e.g., 5-azocytidine). The treated cells are administered to the human. The cell population which is treated with the protein kinase C inhibitor and the DNA methylation inhibitor can further include a cell population which co-expresses telomerase. The method can further include selecting from the treated cells, cells which co-express, CD49c, CD90, at least one cardiac-related transcription factor (e.g., GATA4, Irx4, Nkx2.5) and, optionally, telomerase.

In still another embodiment, the invention includes a method of forming a committed progenitor cell-type, comprising the step of combining a substantially homogenous population of cells which co-expresses CD49c and CD90 with a population of cells that includes at least one committed progenitor cell type. The committed progenitor cell-type can be formed in vitro or in vivo. The formation of the committed progenitor cell-type can be formed in vivo by administering the substantially homogenous population of cells which co-express CD49c and CD90 into a human. For example, the method can be used to form a neuronal cell by combining the substantially homogenous cell population of the invention with a neuronal cell population (e.g., the central or peripheral nervous system).

In a particular embodiment, the population of cells, which are combined with the cells of the invention to form a committed progenitor cell-type, are selected from the group consisting of a population of nerve cells and a population of cardiac muscle cells. In one embodiment, the population of cells which co-express CD49c and CD90 also express telomerase. In yet another embodiment, the population of cells which co-express CD49c and CD90 and, optionally, telomerase, also express at least one cardiac-related transcription factor. In another embodiment, the substantially homogenous population of cells used to form a committed progenitor cell-type are isolated. In a further embodiment, the substantially homogenous population of cells which are employed in the method of forming the committed progenitor cells are a substantially homogenous stem cell population.

An additional embodiment of the invention is a substantially homogenous cell population which co-expresses CD49c, CD90 and has a doubling time less than about 144 hours (e.g., less than about 72 hours, less than about 48 hours, less than about 65 hours, less than about 35 hours) when cultured under a low oxygen condition (e.g., less than about 15% volume oxygen, less than about 10% volume oxygen, less than about 5% volume oxygen).

In still another embodiment, the invention is a substantially homogenous cell population which co-expresses CD49c, CD90 and has a doubling time less than about 144 hours (e.g., less than about 72 hours, less than about 48 hours, less than about 65 hours, less than about 35 hours) when cultured under a low oxygen condition (e.g., less than about 15% volume oxygen, less than about 10% volume oxygen, less than about 5% volume oxygen), wherein the substantially homogenous cell population is formed by a method, comprising the step of culturing a cell population source at a seeding density of about 100 cells/cm$^2$ under the low oxygen condition.

In another embodiment, the invention includes a pharmaceutical composition comprising a substantially homogeneous cell population which co-express CD49c and CD90 (e.g., between about $5 \times 10^5$ to $2 \times 10^6$ cells). In one embodiment, the pharmaceutical composition has at least about $10^5$ substantially homogeneous cells which co-express CD49c and CD90. In another embodiment, the pharmaceutical composition has at least about $10^6$ substantially homogeneous cells which co-express CD49c and CD90. The cells comprising the pharmaceutical composition can also not express CD34 and/or CD45 and/or can express at least one trophic factor selected from the group consisting of BDNF, NGF, NT-3, IL-6, IL-7, IL-11, SCF, MCP-1, matrix metalloproteinase-9 (MMP-9), Cystatin-C and VEGF.

In a further embodiment, the invention includes a pharmaceutical composition comprising a substantially homogeneous cell population which co-express CD49c, CD90 and telomerase.

In yet an additional embodiment, the invention includes a pharmaceutical composition comprising a substantially homogenous cell population which co-express a CD49c, CD90, at least one cardiac-related transcription factor and, optionally, telomerase.

In another embodiment, the invention includes a pharmaceutical composition comprising a substantially homogenous cell population which co-expresses CD49c, CD90, GATA4, Irx4, Nkx2.5 and, optionally, telomerase.

The substantially homogenous cells of the invention which co-express CD49c and CD90; co-express CD49c, CD90 and telomerase; or co-express CD49c, CD90 but does not express BSP, can be administered to a human suffering from a neurological condition. A "therapeutically beneficial amount" of the substantially homogenous population of cells of the invention is a quantity sufficient to enhance neuronal function in a subject having a neurological condition (e.g., spinal cord injury) to be clinically relevant.

The cells of the invention can be, for example, transplanted, placed or administered, for example, in the central nervous system (e.g., brain or spinal cord), peripheral nervous system or cardiac tissue (e.g., cardiac muscle). The site of placement in the nervous system or cardiac tissue for the cells of the invention is determined based on the particular neurological or cardiac condition (e.g., direct injection into the lesioned spinal cord parenchyma, intra-thecal injection, intra-cardiac injection, or intravenous injection). For example, cells of the invention can be placed in or near the substantia nigra of patients suffering from Parkinson's disease. Similarly, cells of the invention can be placed in or near the spinal cord (e.g., cervical, thoracic, lumbar or sacral) of patients suffering from a spinal cord injury. Likewise, cells of the invention can be administered into the cardiac muscle (e.g., ventricular or atrial cardiac muscle) in a patient suffering from a myocardial infarction or other cardiac condition.

The cells of the invention can be placed or transplanted in cavities or spaces of the central nervous system, peripheral nervous system, ventricular space of heart, or atrial space of heart. For example, the cells of the invention can be placed in the ventricles of the brain, subarachnoid space of the spinal cord, vertebral canal of the spinal cord, ventricles or atria of the heart. One skilled in the art would be able to determine the manner (e.g., needle injection or placement, more invasive surgery) most suitable for placement of the cells depending upon the location of the neurological condition and the medical condition of the patient.

In addition, routes of administration of the cells of the invention, or when cells of the invention are admixed with pharmaceutical carriers, encompassed by the present invention include, for example, intramuscular, intravenous, intraarterial, intraperitoneal, subcutaneous routes, oral, or nasal administration.

The substantially homogenous cells of the invention which co-express CD49c and CD90 can be administered alone or as admixtures with conventional excipients, for example, pharmaceutically, or physiologically, acceptable organic, or inorganic carrier substances suitable for enteral or parenteral application which do not deleteriously react with the cells of the invention. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the cells of the invention.

When parenteral application is needed or desired, particularly suitable admixtures for the cells are injectable, sterile solutions, preferably oily or aqueous solutions, as well as suspensions, emulsions, or implants, including suppositories and soaking in GELFOAM®. In particular, carriers for parenteral administration include aqueous solutions of dextrose, saline, pure water, ethanol, glycerol, propylene glycol, peanut oil, sesame oil and polyoxyethylene-block polymers. Pharmaceutical admixtures suitable for use in the present invention are well-known to those of skill in the art and are described, for example, in Pharmaceutical Sciences (17th Ed., Mack Pub. Co., Easton, Pa.) and WO 96/05309 the teachings of both of which are hereby incorporated by reference.

The substantially homogenous population of cells which co-express CD49c and CD90 can be used alone or in any combination when administered to a human suffering from a neurological condition. For example, steroids or pharmaceutical synthetic drugs can be co-administered with the cells of the invention. Likewise, treatment of spinal cord injury can include the administration/transplantation of the cells of the invention in a human whose spine has been physically stabilized.

The dosage and frequency (single or multiple doses) of the administration or transplantation of the cells to a human, including the actual number of cells transplanted into the human, can vary depending upon a variety of factors, including the particular condition being treated (e.g., neurological condition, cardiac condition, such as a myocardial infarction, degenerative condition, acute injury), size, age, sex, health, body weight, body mass index, diet of the human, nature and extent of symptoms of the neurological condition (e.g., early onset Parkinson's disease versus advanced Parkinson's disease; spinal cord trauma versus partial or complete severing of the spinal cord), or cardiac condition (e.g., congestive heart failure, myocardial infarction); kind of concurrent treatment (e.g., steroids); complications from the neurological or cardiac conditions; extent of tolerance to the treatment or other health-related problems.

Humans with a neurological or cardiac condition can be treated for days (e.g., 30) with cells of the invention (e.g., about $10^6$ cells), by a several routes of administration (e.g., intrathecal, intravenous).

It is also envisioned that the methods of the invention can be employed to treat neurological conditions in mammals other than human mammals. For example, a non-human Mammal in need of veterinary treatment, e.g., companion animals (e.g., dogs, cats), farm animals (e.g., cows, sheep, pigs, horses) and laboratory animals (e.g., rats, mice, guinea pigs).

The present invention is further illustrated by the following examples, which are not intended to be limiting in any way.

EXEMPLIFICATION

Example 1

Isolation of a Adherent as Colony Forming Units of Cells or "CFUs" from Bone Marrow Aspirates Following Red Blood Cell Lysis Bone marrow cells were aspirated from the iliac crest of healthy adult human volunteers. The red blood cell component of the aspirate was lysed by mixing the aspirate with an ammonium chloride buffer consisting of 155 mM ammonium chloride, 10 mM potassium bicarbonate and 0.1 mM EDTA (ethylenediaminetetraacetic acid), pH 7.2, at a 1:20 ratio of marrow aspirate to buffer. The resulting cell suspension was vortexed for 2 seconds, incubated for 2 minutes at ambient temperature and then centrifuged (10 minute at 500×g). The resulting mononuclear cell pellet was resuspended in complete medium and centrifuged (10 minutes at 500×g). Complete media is Minimal Essential Medium-alpha (Gibco BRL, Rockville, Md.) supplemented with 4 mM glutamine and 10% sera-lot selected fetal bovine serum (FBS, Gibco BRL, Rockville, Md.). The cell pellet was then re-suspended in the complete medium and centrifuged a second time (10 minutes at 500×g).

The resulting pellet was re-suspended in the complete medium and the number of viable cells was determined by trypan blue-exclusion. The mononuclear cell suspension was then seeded in tissue culture-treated T75 flask at a density of 50,000 cells/cm2 and incubated at 37° C. in an atmosphere consisting of 5% carbon dioxide, 5% oxygen, and 90% nitrogen. On the fifth day of culture, the non-adherent cells and conditioned media (also referred to herein as "spent media") were aspirated from the flasks and the adherent cells re-fed with fresh complete medium. The adherent colony forming units (CFUs) were expanded for an additional 3-5 days.

The generation of CFUs was monitored in 6-well plates concurrently initiated under identical conditions to the T75 flasks. The spent medium was removed from the 6-well plates and the adherent cells were fixed for 5 minutes in 100% methanol, and then stained with methylene blue to visualize the CFUs. An initial seeding density of 75,000 cells/cm$^2$ efficiently generated CFUs. After processing the bone marrow aspirate by either density gradient separation or ammonium chloride lysis, CFU efficiency was dramatically affected by oxygen concentration.

After 7 days in culture, the purity (percentage of cells which co-express CD49c and CD90) of the CFUs generated was determined by flow cytometry. T75 flasks were washed twice with Hank's Balanced Salt Solution (HBSS; CellGro Technologies) and treated with 0.1% Trypsin/1 mM EDTA solution (Life Technologies) for 10 minutes at 37° C. Cultures were removed from incubator and 10 mL of complete medium was added. Cells were triturated from the flask, transferred to a 50 mL centrifuge tube and centrifuged (500×g for 5 minutes). The resulting pellet was resuspended in 10 mL of HBSS.

Figure 1B:
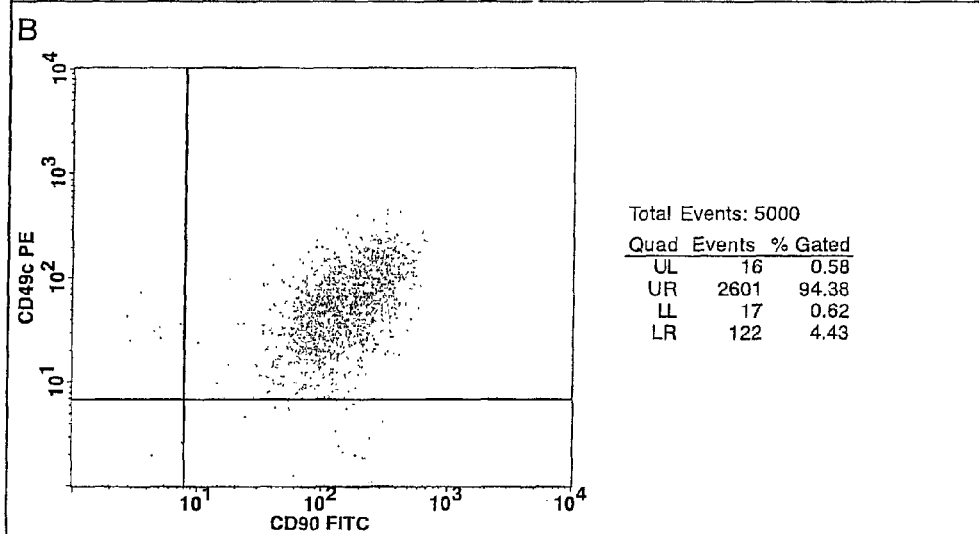

Resuspended cells (approximately 10$^6$) were aliquoted into 12×75 mm Flow Cytometry tubes and repelleted at 500×g for 5 minutes. The HBSS was removed and 25 mL of the following antibodies (all obtained from Becton Dickenson), alone or in combination, were placed into each tube: mouse IgG1k FITC or -PE (clone MOPC 21) CD49c-PE (cl. C3II.1), CD90-FITC (cl. 5E10), CD45-FITC or -PE (cl. HI30). Tubes were gently vortexed and incubated for 30 minutes at 4° C. Cells were then washed in HBSS/1% bovine serum albumin, centrifuged (30 min, 4° C.) and the resulting cellular pellet fixed by the addition of 250 microliters of 2% paraformaldhyde/HBSS. Flow cytometric analysis was performed employing a Becton Dickenson FACSVantage SE cytometer and analyzed using CELL-QUEST® software. FIG. 1 depicts results representing data collected from 2,500-10,000 events per panel. After compensation for non specific antibody staining using mouse IgG1 isotype controls, cellular expression of CD45, CD49c and CD90 in the cultured bone marrow cells was assessed. The adherent population derived from mononuclear cells initially purified using ammonium chloride lysis contained approximately 70% CD49c positive cells at a similar stage of culture (FIG. 1A). The majority of cells that did not express CD49c were positive for expression of hematopoetic/myeloid lineage marker CD45 (FIG. 1A, LR quadrant), demonstrating that the CD49c positive cell population derived from human bone marrow isolated was not directly related to known hematopoietic precursors. More than 94% of the adherent population was CD90 and CD49c positive (FIG. 1B).

Example 2

Isolation of a Adherent CFUs from Bone Marrow Aspirates Following Density Separation Bone marrow cells were aspirated from the iliac crest of healthy adult human volunteers. The bone marrow aspirate was diluted with calcium and magnesium free phosphate buffered saline (PBS) to achieve a mononuclear cell concentration of 7×10$^6$ cells/mL and overlaid onto an equal volume of HISTOPAQUE® 1.119 (Sigma, St. Louis, Mo.) and centrifuged (30 min at 700×g). The resulting mononuclear cell fraction was transferred to a clean centrifuge tube containing PBS and centrifuged (10 minutes at 500×g). The cell pellet was re-suspended in PBS and centrifuged (10 minutes at 500×g). The supernatant was aspirated from the cell pellet and the cells re-suspended in complete media.

The number of viable cells in the resulting cell suspension was determined by trypan blue-exclusion. The cell suspension was then seeded in tissue culture-treated T75 flasks at a density of 50,000 cells/cm$^2$ and incubated at 37° C. in an atmosphere of 5% carbon dioxide, 5% oxygen and 90% nitrogen. On the fifth day of culture, the non-adherent cells and conditioned media (also referred to herein as "spent media") was aspirated from the flasks and the adherent cells re-fed with fresh complete medium. The adherent CFUs were expanded for an additional 3-5 days.

Figure 2A:
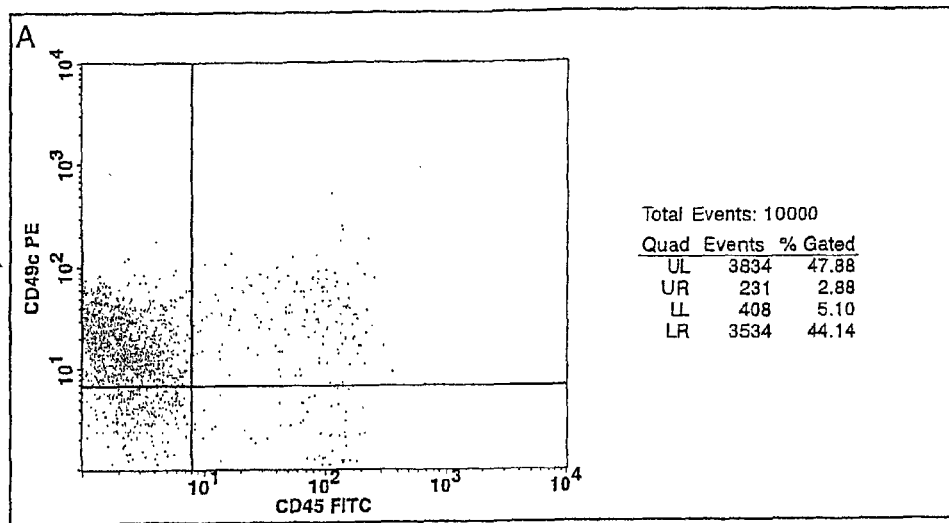
FIGS. 2A, 2B, and 2C illustrate the flow cytometric analysis of cell populations in the Primary (2A) and Master (2B and 2C) Cell Banks generated from a bone marrow aspirate following density separation.
Figure 2B:
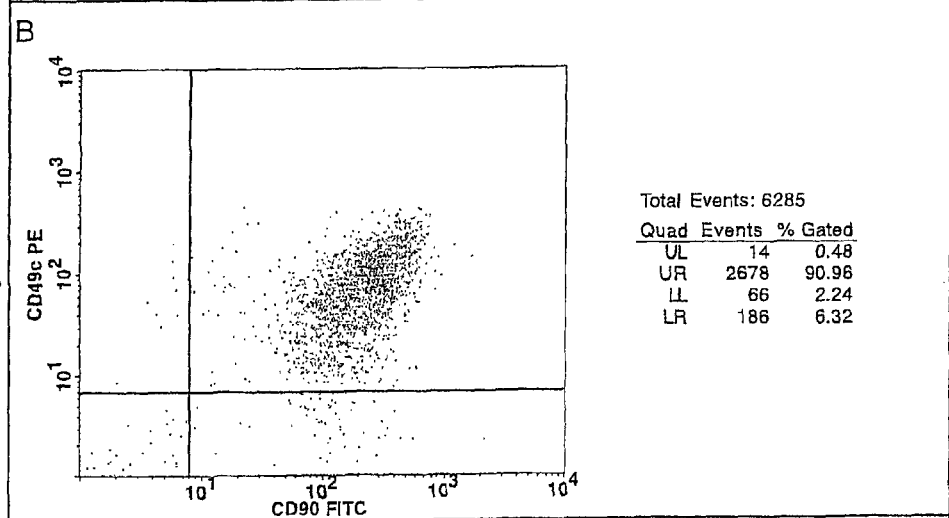

Cytometry analysis of the CFU generated showed that approximately 50% of the adherent population expressed the marker CD49c at 7 days in vitro (FIG. 2A, sum of UL and UR quadrants). The majority of cells that did not express CD49c were positive for expression of hematopoetic/myeloid lineage marker CD45 (FIG. 2A, LR quadrant), demonstrating that the CD49c positive cell population derived from human bone marrow isolated by this procedure was not directly related to known hematopoietic precursors. More than 91% of the adherent population was CD90 and CD49c positive (FIG. 2B).

Example 3

Production of Primary and Master Cell Banks from CFUs

After 7-10 days in culture, the CFUs generated using the methods described in Example 1 were removed from the T75 flasks with a 0.25% trypsin/1 mM EDTA solution (Life Technologies). After 10 minutes at 37° C., the trypsin was inactivated with 10 mL of complete medium. The cells were washed once with HBSS and re-suspended in Glycerol Cell Freezing Medium® (Sigma Chemical Co.). Aliquots (referred to herein as the "Primary Cell Bank," or "Seed Cell Bank") of the suspension consisting of $4.0 \times 10^5$ cells/vial were cooled with liquid nitrogen vapor at 1° C./minute using a CryoMed (Form a) controlled rate freezer and the stored in a Cryo Plus liquid nitrogen storage tank (Form a).

An aliquot of cells was removed from the Primary Cell Bank and cultured at a density of 30 cells/cm$^2$ in 500 cm$^2$ tissue culture-treated plates (Corning) in complete medium and incubated at 37° C. in an atmosphere consisting of 5% carbon dioxide, 5% oxygen, and 90% nitrogen. After two weeks of culture, cells were removed from the plates with trypsin and were cryopreserved at $4.0 \times 10^5$ cells/vial (referred to herein as the "Master Cell Bank," or "Production Cell Bank").

Figure 1C:
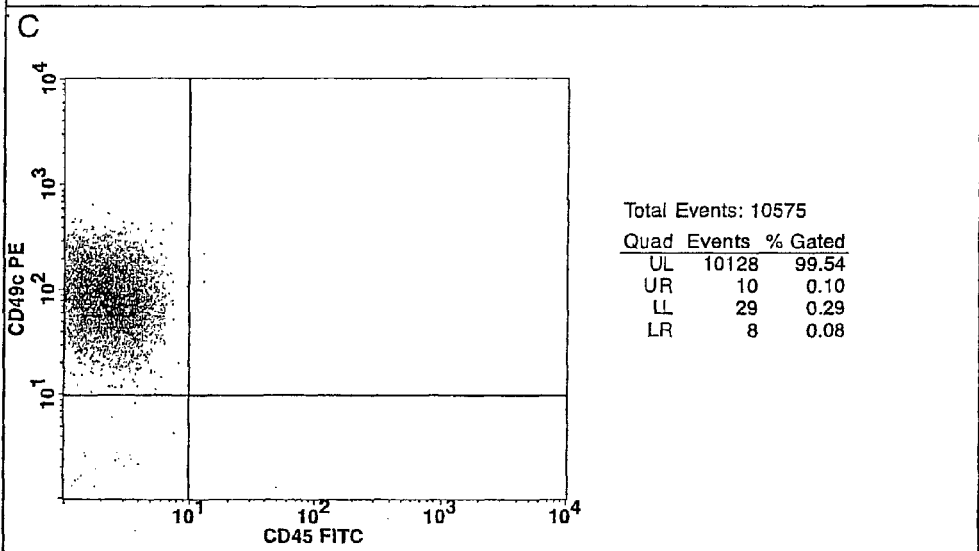

The purity of the cells (percentage of cells which co-express CD49c/CD90) in the Master Cell Bank was determined by flow cytometry using the same method as above. The vast majority (>98%) of the resulting population expressed CD49c (FIG. 1C) and virtually lacked any expression of the myeloid related marker CD45 (FIG. 1C, LR quadrant). Thus, the expansion procedure as described herein produces a substantially homogenous population of adherent cells which co-express CD49c and CD90 and lack significant expression of the marker CD45.

Figure 2C:
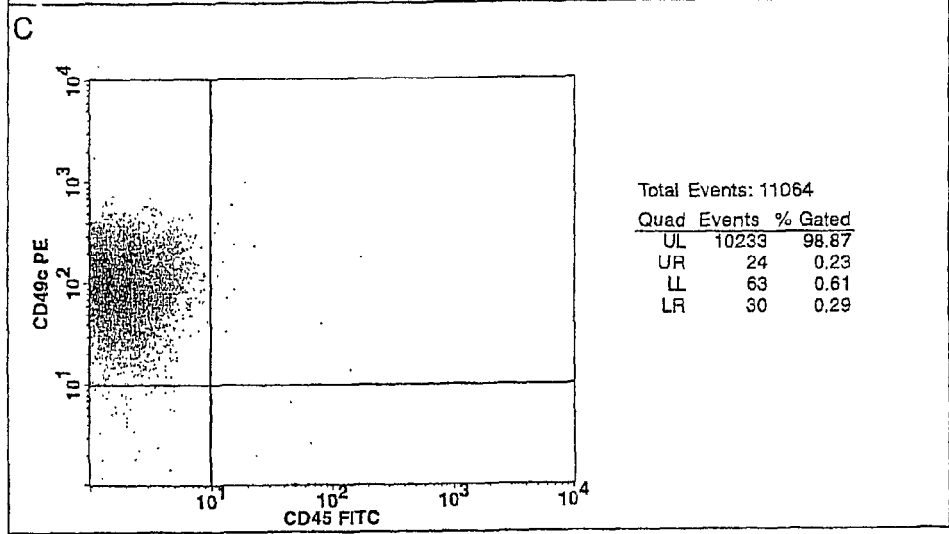

Similarly, the master cell bank generated from the CFU derived using the method of Example 2 showed that and the majority of cells (>98.8%) of the resulting cell population expressed CD49c (FIG. 2C) and virtually lacked any expression of the myeloid-related marker CD45 (FIG. 2C, LR quadrant). Thus, the expansion procedure as described herein generates a substantially homogenous population of adherent cells which co-express CD49c and CD90 and lack significant expression of the marker CD45.

Example 4

Expansion Capability of the Cell Population which Co-Express CD49c and CD90

A Primary Cell Bank of CFUs was derived from 25 mLs of bone marrow aspirate and stored as frozen aliquots using the methods of Examples 1 and 2. An aliquot was thawed, expanded and frozen to generate the Master Cell Bank as described in Example 3. An aliquot of cells was removed from the Master Cell Bank and cultured at a density of 30 cells/cm$^2$ in 500 cm$^2$ tissue culture-treated plates (Corning) in complete medium and incubated at 37° C. in an atmosphere consisting of 5% carbon dioxide, 5% oxygen, and 90% nitrogen. After two weeks of culture, cells were removed from the plates with trypsin and cryopreserved at $2\text{-}10 \times 10^6$ cells/vial. The process was repeated in succession to produce additional Cell Banks of cells which co-express CD49c and CD90.

Figure 3:
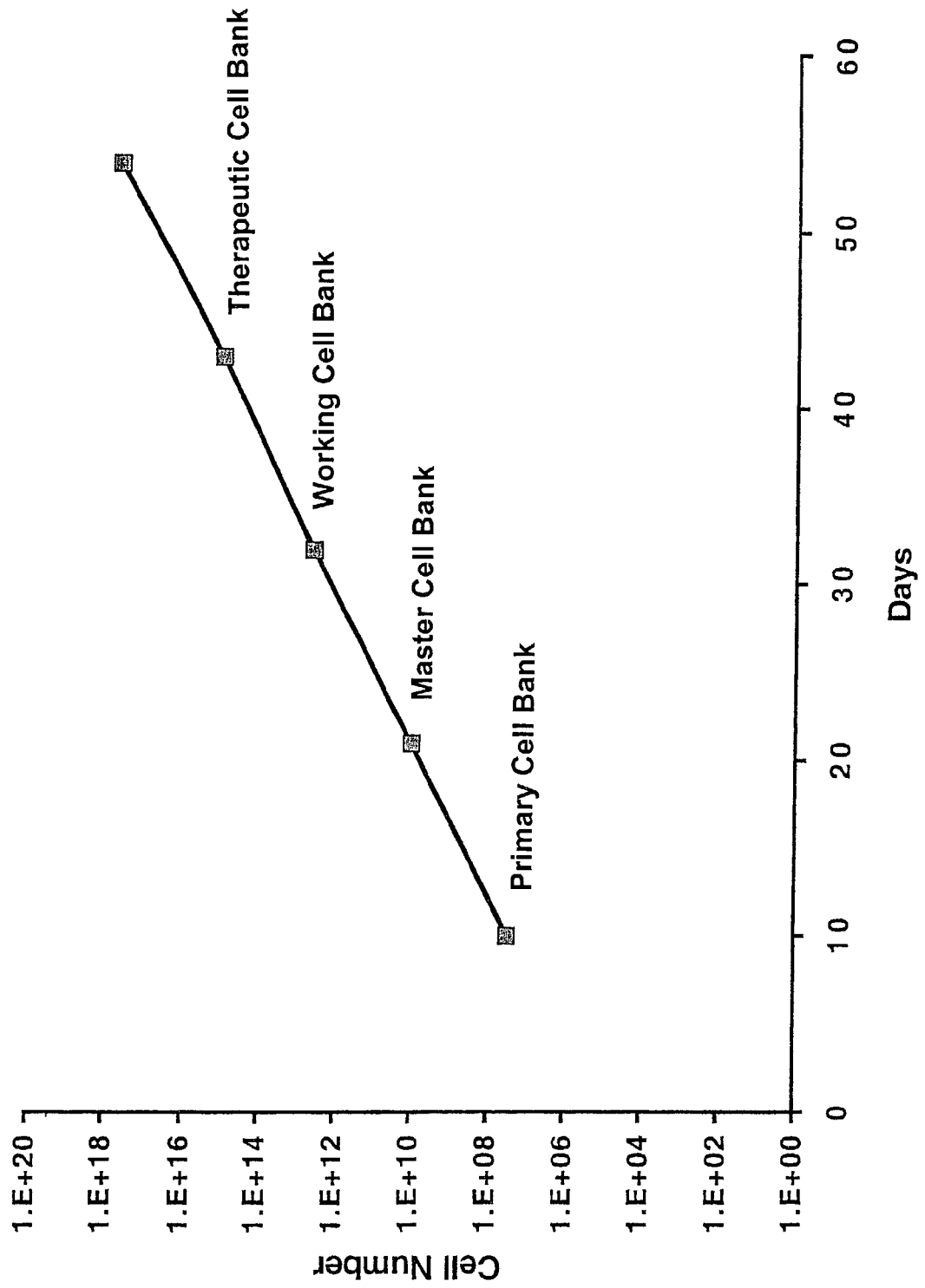
FIG. 3 illustrates the yield (Cell Number) of cells that co-express CD49c and CD90 cells during ex vivo expansion of a Primary Cell Bank of colony forming units (CFUs) derived from human bone marrow aspirates.
Figure 4:
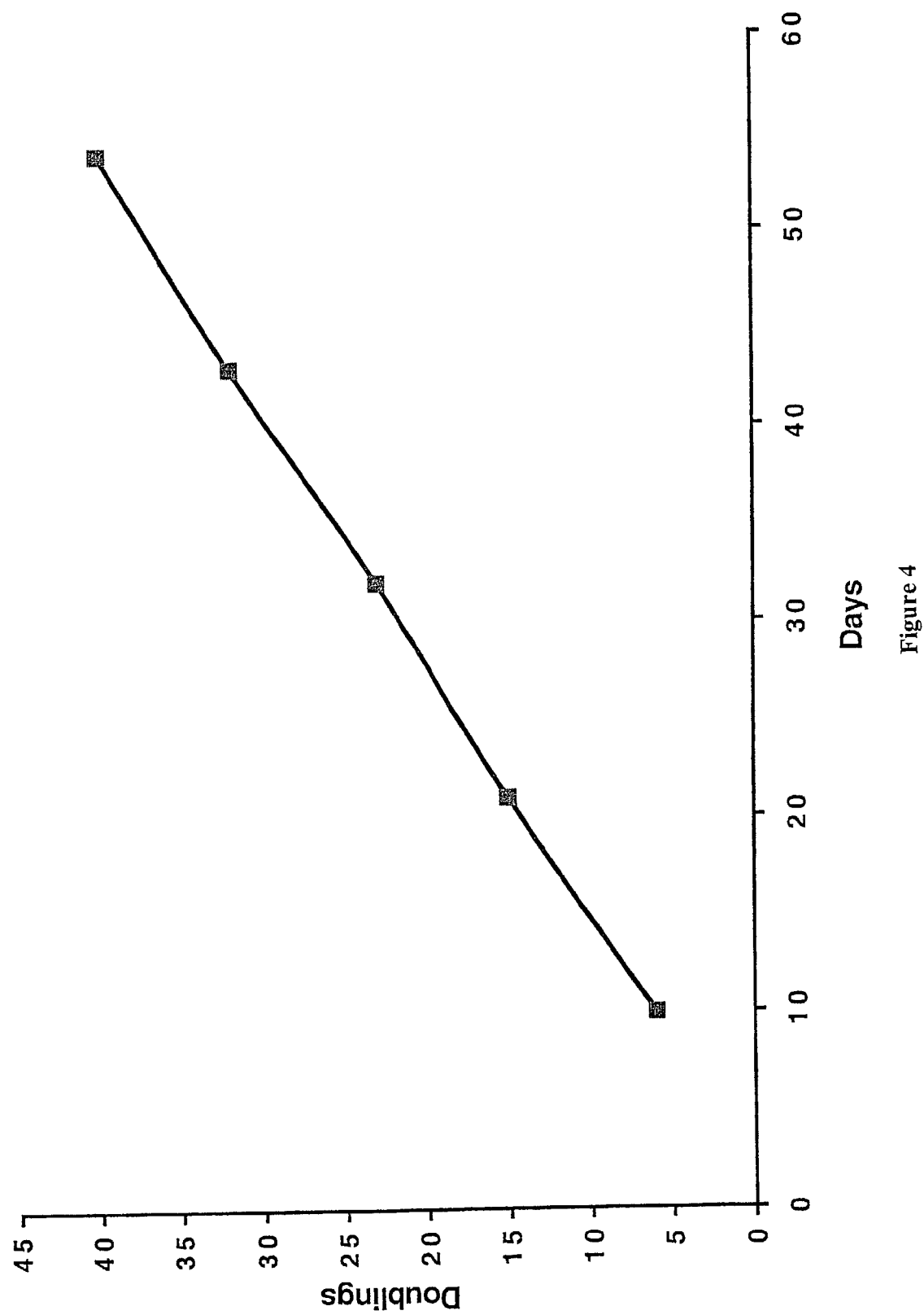
FIG. 4 illustrates the doubling rate of cell populations that co-express CD49c and CD90 cell population in culture.

The cell number generated from a single aliquot at the end of each successive expansion was determined by trypan exclusion and multiplied by the number of aliquots to calculate the yield (FIG. 3). Four successive expansions can potentially generate up to $1 \times 10^{17}$ cells from 25 mLs of bone marrow aspirate obtained from a single donor. The number of cell doublings was calculated from the cell yields using the following formula: (Log(end cell #)–Log(starting cell #)/Log(2) ("(2)" denotes doubling). The cell population underwent about 8 doublings during each expansion (FIG. 4). The doubling rate (# days in culture×24/doublings) was 30 hrs and remained constant for at least 50 doublings. Even after 30 doublings, the population uniformly retained the characteristic morphology of small, dividing cells without apparent evidence of the enlarged, flat morphology of aged or terminally-differentiated cells.

Example 5

Expression of Transcripts Encoding Regulators of Cell Growth and Osteoblast Differentiation by Cell Populations which Co-Express CD49c and CD90

The expression of transcripts for telomerase, p21, p53, CBFA1 and BSP were determined using quantitative polymerase chain reaction (qPCR). Briefly, Master Cell Bank of CFUs were derived from a bone marrow aspirate and stored as frozen aliquots using the method of Example 1. An aliquot was thawed, cultured at a density of 30 cells/cm$^2$ in tissue culture-treated T75 flasks in complete medium and incubated at 37° C. in an atmosphere consisting of 5% carbon dioxide, 5% oxygen, and 90% nitrogen.

After two weeks of culture, the cells were seeded in 96 well plates at 3000 cells/well. RNA was isolated using the QIAGEN RNeasy reagents and the Qiagen Biorobot 3000. An aliquot of the eluted RNA was used to synthesize cDNA. RNA was mixed with Promega MMLV, dNTPS, decamers and RNasin and incubated at 37° C. for 1 hour, followed by heat inactivation. For quantitative PCR (qPCR), cDNA samples were combined with Applied Biosystems SYBR Green PCR Core reagents and amplicon specific primers, as described below, in a 384 well format. The 384 well plate was then transferred to the Applied Biosystems ABI Prism 7900 for qPCR analysis. The qPCR program entailed a 2 minute cycle at 50° C., followed by a 10 minute cycle at 95° C. to activate the polymerase. This was than followed by 40 amplification cycles consisting of 15 seconds of melting at 95° C. and one minute of extension/annealing at 60° C.

Cycle threshold values were converted into relative transcript number using a standard curve then normalized using the corresponding 18s. Data are expressed as a ratio of transcript per $10^6$ 18s transcripts. The name, Genbank ID, by location and sequence of the qPCR primers are as follows:

```
18s-1F,    K03432,    1742-1760 bp,5'-ATG GGG ATC GGG GAT TGC A-3';      (SEQ ID NO: 1)

18s-1R,    K03432,    1871-1890 bp,5'-CCG ATC CGA GGG CCT CAC TA-3';     (SEQ ID NO: 2)
```

```
BSP-1F,    NM000582,   483-508 bp,    5'-CAC TCC AGT TGT CCC CAC AGT AGA CA3';    (SEQ ID NO: 3)

BSP-1R,                611-632 bp,    5'-TCG CTT TCC ATG TGT GAG GTG A-3';        (SEQ ID NO: 4)

CBFA1-1F,  L40992,     389-407 bp,    5'-GGC CGG AGT GGA CGA GGC AA-3';           (SEQ ID NO: 5)

CBFA1-1R,  L40992,     504-529 bp,    5'-CAT CAA GCT TCT GTC TGT GCC TTC TG-3';   (SEQ ID NO: 6)

p21-1F,    S67388,      52-72 bp,     5'-ACC GAG GCA CTC AGA GGA GGC-3';          (SEQ ID NO: 7)

p21-1R,    S67388,     171-191 bp,    5'-GCC ATT AGC GCA TCA CAG TCG-3';          (SEQ ID NO: 8)

p53-qFP4,  M14694,     521-545 bp,    5'-GAT GTT TTG CCA ACT GGC CAA GAC C-3';    (SEQ ID NO: 9)

p53-qRP4,  M14694,     674-698 bp,    5'-AGG AGG GGC CAG ACC ATC GCT ATC T-3';    (SEQ ID NO: 10)

Telo-1F;   AF015950,   1500-1525 bp,  5'-ACA ACG AAC GCC GCT TCC TCA GGA AC-3';   (SEQ ID NO: 11)
and Telo-1R,   AF015950,   1625-1650 bp,  5'-GCC GGA ACA CAG CCA ACC CCT GG-3'.       (SEQ ID NO: 12)
```

Telomerase activity is necessary for maintaining telomeres, which are DNA sequences located at the ends of chromosomes. Since most human cells lack telomerase, the telomeres shorten with each division until the cells growth arrest (Harley, C. B., *Mutation Research* 256(2-6):271-282 (1991); Hara, E. et al., *Biochem Biophys Res Commun* 179(1):528-534 (1991); Shay, J. W. et al., *Exp Cell Res* 196(1):33-39 (1991)). Cell populations which co-express CD49c and CD90 express telomerase at the level of approximately 13 transcripts/$10^6$ transcripts of 18S rRNA, which is consistent with the finding that this cell population continued to proliferate at a constant rate.

The p53 tumor suppressor plays a key role in the cell's response to DNA damage and inactivation of this gene is an important step in carcinogenesis. p53 expression is upregulated in response to DNA damage. Its ability to prevent the proliferation of defective cells involves the activation of several growth arrest genes including p21 (Burns, T. F. et al., *Oncogene* 20(34):4601-4612 (2001)). The substantially homogenous cell population of the invention which co-express CD49c and CD90 expressed about 670 p53 transcripts/$10^6$ transcripts of 18S rRNA. This level of p53 shows that the tumor suppressor p53 was not induced.

p21 is a potent cell cycle inhibitor and its expression during the cell cycle is tightly regulated at the transcriptional level (Gartel, A. L. et al., *Exp Cell Res* 246(2):280-289 (1999)). p21 is induced in growth arrested cells in response to oxidative stress in addition to DNA damage (Yin, Y., et al., *Mol Carcinog* 24(1):15-24 (1999)). The substantially homogenous cell population of the invention which co-express CD49c and CD90 expressed p21 about 1690 transcripts/$10^6$ transcripts of 18s rRNA. This level of p21 shows that p21 was not induced and is consistent with both a low level of p53 and the short doubling time measured in Example 4.

The transcription factor, CBFA1, is necessary for osteoblast differentiation and bone formation (Otto, F., *Cell* 89(5):765-771 (1997)). Bone sialoprotein (BSP) is a prominent, mineral-associated protein in the extracellular matrix of bone and is expressed by fully differentiated osteoblasts (Benson, M.D., et al., *J Biol Chem* 275(18):13907-13917 (2000)). The substantially homogenous cell population of the invention which co-express CD49c and CD90 expressed about 130 CBFA1 transcripts/$10^6$ transcripts of 18S rRNA and BSP was absent, which show that the cell population of the invention represents a progenitor that has not significantly differentiated into osteoblasts. Osteoblast differentiation is described in Ducy, P., *Dev Dyn* 219(4):461-471 (2000)).

Example 6

Secretion of Neurotrophic Factors and Cytokines by a Substantially Homogenous Cell Population which Co-Express CD49c and CD90.

An aliquot of the Master Cell Bank generated in Example 1 was thawed and plated onto T75 flasks at 2500 cells/cm$^2$ with complete medium and incubated at 5% $O_2$. The following day the medium was removed and replaced with fresh complete medium. The supernatant was collected 8 hours later from T75 and the cells were counted (Cell count=280,000 cells). The supernatant was aliquoted to 1 ml tubes and stored at −20° C. Another T75 was processed the same way 3 days later (Cell count =2.43 million). Supernatants were later thawed at room temperature and assayed by ELISA for secretion of the following neurotrophic factors/cytokines using commercially available kits: BDNF (Chemicon), NGF (Chemicon), MCP-1 (R and D Systems), and IL-6 (R and D Systems). Multiple dilutions were performed on supernatant to ensure that measured values fell within standard ranges of the assay. In addition, media obtained from control cells secreting previously determined amounts of cytokine were run in parallel to assure assay validity. Values were obtained by normalizing raw data derived from ELISA to standard time (24 hours) and cell number (1 million) and are thus expressed as "picograms of cytokine secreted per 1 million cells per 24 hour period as follows:

| Cytokine | Amount Secreted (pg/$10^6$ cells/day) |
|---|---|
| MCP-1 | 1009.15 |
| IL-6 | 18567.60 |
| BDNF | 8.88 |
| NGF | 80.12 |

Example 7

Transplantation of a Substantially Homogenous Cell Population of the Invention which Co-Express CD49c and CD90 into an Acute Rat Spinal Cord Injury Model Following traumatic injury to the spinal cord neuronal death, inflammation and progressive loss of damaged neurons ensue overtime. A substantially homogenous cell population of the invention which co-express CD49c and CD90 improved outcome during acute neurologic injury. A cell population prepared as described in Example 1 was transplanted into contused spinal cord of adult female Sprague-Dawley rats.

The thoracic spinal cord of Sprague-Dawley rats was exposed by laminectomy at the level of T10 under general anesthesia. After the laminectomy is completed, a 10 gm rod was dropped from a height of 25 mm to produce a spinal cord injury of moderate severity onto the exposed spinal cord using the NYU spinal cord impactor (Constantini, S. et al., *J Neurosurg* 80(1):97-111 (1994)). During surgery, the body temperature of the rats was kept at 37° C. During recovery, rats were placed overnight in a temperature and humidity controlled chamber. Seven days after impact injury, the spinal cords were re-exposed. Using a 50 mL gas tight Hamilton syringe (VWR Scientific Products, Bridgeport, NJ) with a 30 gauge needle, 250,000 cells of the invention at a concentration of 25,000/μl were transplanted into the spinal cord. The cells were injected into the epicenter of the syrninx at the T10 level at a rate of 2 mL/minute. The needle was left in place for additional 5 minutes before it was removed from the spinal cord. Following surgery, all animals received 30 mg/kg methylprednisolone intravenously (i.v.) immediately following surgery. To prevent immun-rejection, Cyclosporin A (CsA) was given subcutaneously at 10 mg/kg 3 days prior to the day of transplantation and maintained thereafter.

Figure 5:
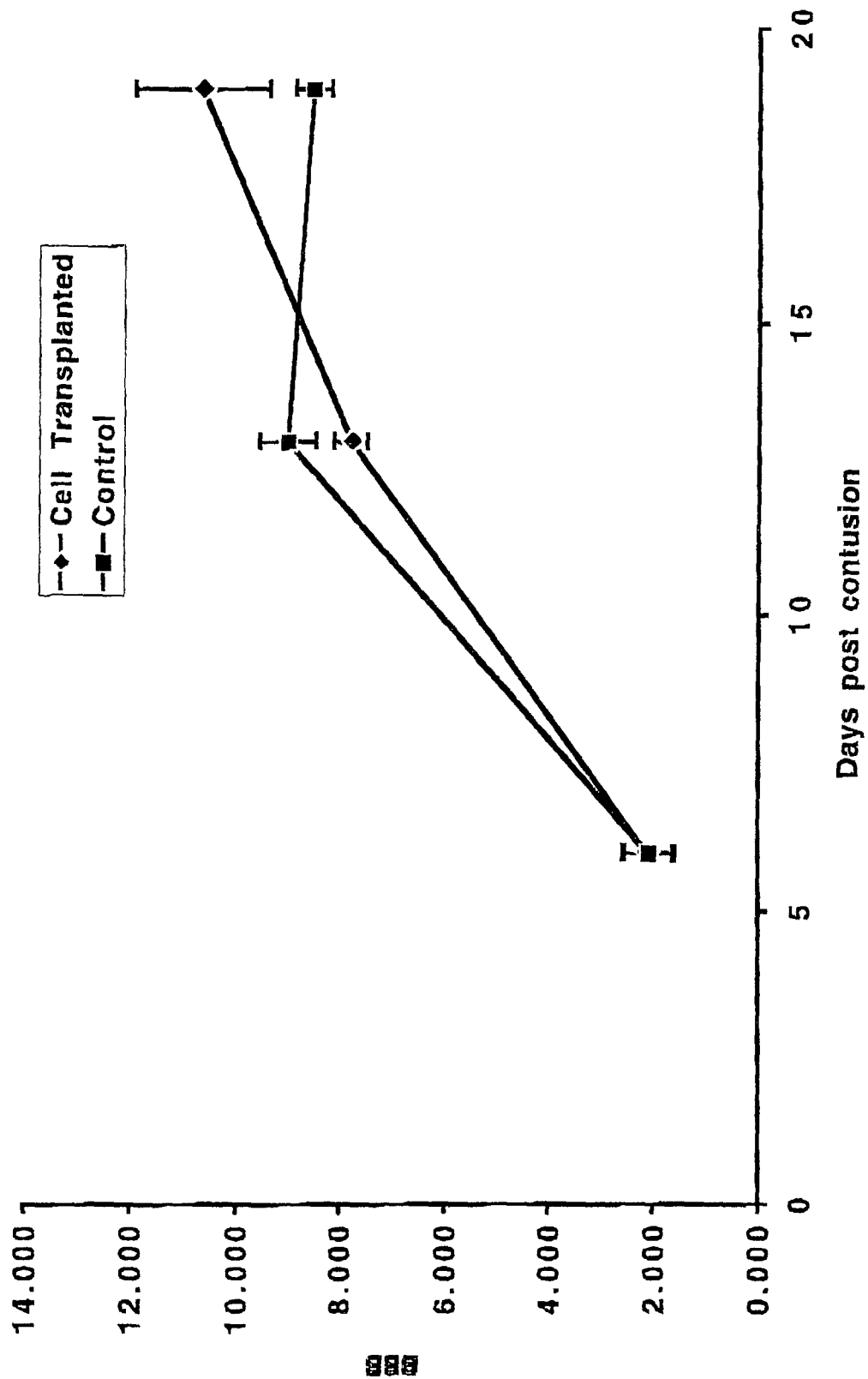
FIG. 5 illustrates the Basso-Beattie-Bresnahan (BBB) index for rats following spinal cord injury and after transplantation with a substantially homogenous cell population which co-express CD49c and CD90. At 19 days post contusion, rat received the cell transplantation showed greater improvement than rat received only PBS control.

The Basso-Beattie-Bresnahan openfield locomotor test (BBB Test) (Basso, D. B. et al., *J Neurotrauma* 12(1):1-21 (1995)) were performed the day before transplantation (day 6 after injury). Behavioral testing was performed for each hindlimb weekly using the BBB scores. Scoring was performed blinded to the treatment status. At 19 days after contusion, animals that had received a substantially homogenous population of cells which co-express CD49c and CD90, showed greater improvement on the BBB score than animals received only PBS (10.6±1.2 vs 8.5±0.3) (FIG. 5).

At 2 weeks after transplantation, contused spinal cords from some animals were removed and examined for evidence on nerve fiber regeneration. SMI 32 (Sternberger Monoclonals, Inc, Lutherville, Md.) antibody was used to immunostain for regenerating fibers in the syrinx at a dilution of 1:4000. Numerous fibers were observed growing into the contused syrinx.

Example 8

Expression of Transcripts Encoding Regulators of Neuronal Differentiation by a Substantially Homogenous Population of Cells which Co-Express CD49c and CD90

The expression of transcripts for Sox-2 and Musashi were determined using quantitative polymerase chain reaction (qPCR). Briefly, Master Cell Bank of CFUs were derived from a bone marrow aspirate and stored as frozen aliquots using the method of Example 1. An aliquot was thawed and the cells were seeded in 96 well plates at 2000 cells/well in complete media and incubated at 37° C. in an atmosphere consisting of 5% carbon dioxide, 5% oxygen and 90% nitrogen for 3 days. On the third day of culture, cells were treated with 5 μM nifedipine (an L-type calcium channel blocker). After 24 hours of treatment, RNA was isolated using the QIAGEN®RNeasy reagents and the Qiagen Biorobot 3000. An aliquot of the eluted RNA was used to synthesize cDNA. Specifically, RNA was mixed with Promega MMLV, dNTPS, decamers and RNasin and incubated at 37° C. for 1 hour, followed by heat inactivation.

For quantitative PCR, cDNA samples were combined with Applied Biosystems SYBR Green PCR Core reagents and amplicon specific primers, as described below, in a 384 well format. The 384 well plate was then transferred to the Applied Biosystems ABI Prism 7900 for qPCR analysis. The qPCR program entailed a 2 minute cycle at 50 degrees, followed by a 10 minute cycle at 95 degrees to activate the polymerase. This was then followed by 40 amplification cycles consisting of 15 seconds of melting at 95 degrees and one minute of extension/annealing at 60 degrees. Cycle threshold values were converted into relative transcript number using a standard curve then normalized using the corresponding 18s. Data are expressed as a ratio of transcript per $10^6$ 18s transcripts.

The name, Genbank ID, by location and sequence of the qPCR primers are as follows:

```
18s-1F,       K03432,    1742-1760 bp, 5'-ATG GGG ATC GGG GAT TGC A-3';            (SEQ ID NO:1)

18s-1R,       K03432,    1871-1890 bp, 5'-CCG ATC CGA GGG CCT CAC TA-3';           (SEQ ID NO:2)

Sox-2F,       Z31560,     517-541 bp,  5'-GGC AGC TAC AGC ATG ATG CAG GAC C-3';    (SEQ ID NO:13)

Sox-2R,                   624-647 bp,  5'-CTG GTC ATG GAG TTG TAC TGC AGG-3';      (SEQ ID NO:14)

Musashi-1F,   AB012851,   370-389 bp,  5'-CAA GAT GGT GAC TCG AAC GA-3';           (SEQ ID NO:15)

Musashi-1R,               480-499 bp,  5'-GGT TTT GTC AAA CAT CAG CA-3'.           (SEQ ID NO:16)
```

Musashi-1R, 480-499 bp, 5'-GGT TTT GTC AAA CAT CAG CA-3' (SEQ ID NO:16).

The gene Sox-2 encodes a conserved nuclear transcription factor related to the Mammalian Testis Determining Gene that is expressed throughout the neural tube during brain development and is essential for the survival of primitive neural ectoderm (Uwanogho, *Mech. Dev.* 49:23-36 (1995)). In addition, expression of Sox-2 persists beyond development in restricted populations of adult neural stem cells, suggesting a further role for this factor in regulating neural fate (Zappone, *Development* 127:2367-2382 (2000)). Under unstimulated conditions in complete media, the cells which co-expressed CD49c and CD90 expressed approximately 4 Sox-2 transcripts/$10^6$ transcripts of 18S RNA. However, in response to nifedipine, the cells which co-expressed CD49c and CD90 expressed 28 Sox-2 transcripts/$10^6$ transcripts of 18S RNA, an approximate 7-fold increase. This increase in Sox-2 expression suggests that, in response to certain epigenetic treatments, the cells which co-expressed CD49c and CD90 can display traits associated with early neural populations.

The gene Musashi encodes an RNA-binding protein that is highly expressed within the developing nervous system and, like Sox-2, is also expressed in mammalian neural stem cells (Sakakibara, *Dev Biol* 176:230-242 (1996)). Furthermore, expression of Musashi is required for normal development of multiple neuronal population (Nakamura, *Neuron* 13:67-81 (1994)). Under unstimulated conditions in complete media, the cells which co-expressed CD49c and CD90 expressed approximately 0.005 Musashi transcripts/$10^6$ transcripts of 18S RNA. However, in response to 24 hours of stimulation with nifedipine, the cells which co-expressed CD49c and CD90 expressed 0.093 transcripts/$10^6$ transcripts of 18S RNA, an approximate 17-fold increase. This increase in Sox-2 expression suggests that, in response to certain epigenetic treatments, the cells which co-expressed CD49c and CD90 can display traits associated with early neural populations.

Example 9

The Effect of Intra-Cardiac Injection of Human Adult Bone Marrow Stem Cells (hABM-SC) on Myocardial Infarction The ability of hABM-SCs in restoring cardiac function after direct intra-cardiac injection in a rat animal model induced with experimental myocardial infarct was determined. The distribution and disposition of the hABM-SCs in these animals can be determined.

Materials and Methods

Early-Myocytic Determined Cells (EMD) for Intra-Cardiac Injection hABM-SC were cultured under conditions which induce the expression of cardiac-related transcription factors to produce early-myocytic determined cells. Early-myocytic determined cells were obtained by culturing hABM-SCs in the presence of a DNA methylation inhibitor (e.g., azacytidine) and a protein kinase C inhibitor (e.g., chelerythrine). The early-myocytic determined cells of the invention co-express CD49c, CD90 and at least one cardiac-related transcription factor such as Nkx2.5, Irx4 and GATA4.

"Early-myocytic determined cells ("EMD")," as used herein, refers to cells that are partially differentiated into cardiomyocytes. Criteria to determine whether a cell is an early-myocytic determined cell include, for example, expression of at least one cardiac-related transcription factor by the cell. The early-myocytic determined cells can become cardiac cells (e.g., cardiac muscle cells, also referred to herein as cardiomyocytes).

Cardiomyogenesis, the development or differentiation of cardiomyocytes, is characterized by a time-specific and distribution-specific expression of various proteins and genes. The gene Nkx2.5/CSX (cardio specific homeobox) has been identified as one of the earliest genes expressed during heart development, followed closely by another homeobox gene, the Iroquois homeobox gene4 (Irx4) (Bao, Z., et al., *Science* 283: 1161-1164 (1999); Auda-Boucher, G., et al., *Dev. Biol.* 225: 214-225 (2000)). The transcriptional regulator, GATA-binding transcription factor 4 (GATA4), is abundant in the heart and important in myocyte differentiation (Auda-Boucher, G., et al., *Dev. Biol.* 225:214-225 (2000)). Co-expression of Nkx2.5, Irx4 and GATA4 is unique to cardiac muscle cells (Mably, J. D., et al., *Circulation Rec.* 79(1):4-13 (1996)). Co-expression of transcripts for Nkx2.5, Irx4 and GATA4 in hABM-SC was achieved by culturing hABM-SCs under the following conditions:

Master Cell Bank cells were cultured in a 96 well format in complete medium and incubated at 37° C. in an atmosphere consisting of 5% carbon dioxide, 5% oxygen and 90% nitrogen. After 2 days in culture, cells were cultured in the presence of 30 µM 5-azacytidine (a DNA methylation inhibitor) and 5 µM chelerythrine (a protein kinase C inhibitor) for 3-7 days in complete media. Other protein kinase C inhibitors, such as H-7 dihydrochloride, K252a, staurosporine, bisindolylmaleimide I-V, and calphostin C, can also employed in the methods and culture conditions of the invention to produce early-myocytic differentiated cells. In addition, other DNA methylation inhibitors, such as 5-aza-2-deoxycytide, 5-aza-guanine, 5-aza-2-deoxyguanine, can also be used in the methods and culture conditions of the invention to produce early-myocytic differentiated cells.

After 2 days of culturing in the presence of azacytidine and chelerythrine, RNA was isolated from the cells in culture. An aliquot of the eluted RNA was used to synthesize cDNAs for analysis of the expression of cardiac-related transcription factors. RNA was mixed with Promega Moloney Murine Leukemia Virus (MMLV) reverse transcriptase. cDNAs, dNPTs, decamers and RNasin were incubated for about 1 hour at about 37° C., followed by heat inactivation. For quantitative polymerase chain reaction (qPCR), cDNA samples were combined with Applied Biosystems SYBRR GREEN PCR 2× MASTER MIX® and amplicon specific primers in a 384 well format. The ABI PRISM 7900 HT® performed the qPCR using a standard program of about 2 minutes at about 50° C., about 10 minutes at about 95° C., about 40 amplification cycles consisting of about 15 seconds of melting at about 95° C. and one minute of annealing/extension at about 60° C. Cycle threshold values were converted into relative transcript number using a standard curve and then normalized to the corresponding 18s RNA transcripts. Data were expressed as a ratio of transcript per $10^6$ 18s RNA transcripts. Control values for transcripts evaluated were in the range of 0.001-0.003. GATA4 was induced to 0.71 transcripts, Irx4 to a level of 0.023 transcripts and Nkx2.5 to 0.023 transcripts, all relative to $10^6$ 18s RNA. Cells which expressed at least one cardiac-related transcription factor, e.g., GATA4, Irx4 and Nkx2.5, are early-myocytic determined cells or early-myocytic determined hABM-SCs.

Early-myocytic determined cells, which co-express GATA4, Irx4 and Nkx2.5, were plated at about 30 cells/cm² with complete media and incubated at about 37° C. in an atmosphere consisting of about 5% carbon dioxide, about 5% oxygen and about 90% nitrogen. After 7 days in culture all media was replaced with new complete media containing 30 µM 5-azacytidine and 5 µM chelerythrine and cells cultured for about 3 days followed by a complete media change and cultured an additional 7 days. Early-myocytic determined cells had a doubling time about twice that of unmodified cells. The early-myocytic determined cells can secrete trophic factors such as IL-6, VEGF, MCPI and BDNF.

Unmodified Cells for Intra-Cardiac Injections

Donor 059-derived hABM-SCs, which were not cultured in the presence of a DNA methylation inhibitor (e.g., 5-azacytidine) and a protein kinase C inhibitor (e.g., chelerythrine chloride) are referred to herein in this example as "unmodified hABM-SCs" or "unmodified cells." Unmodified hABM-SCs were a substantially homogenous cell population which co-expressed CD49c, CD90 and telomerase; and were prepared as described in Examples 1-8.

Experimental Induction of Myocardial Infarction

Myocardial infarction was experimentally induced in male and female Sprague-Dawley rats (age about 3 months) by placement of a permanent silk ligature around the left-anterior descending (LAD) coronary artery through a midline sternotomy according to established methods (Müller-Ehmsen, J. et al., *Circulation* 105:1720-1726 (2002)). Five days after the procedure, rats were treated with a standard regimen of 10 mg/kg Cyclosporine A treatment that lasted for the duration of the 4 week study.

About seven to eight days after induction of the infarction, rats were anesthetized, intubated and an intercostal incision was made to expose the apex of the heart. An ultrasonic Millar catheter was inserted through the ventricular wall, and pressure over time measurements, dp/dt, obtained for about 30-60 seconds. This model of infarct production and pressure/time measurements of cardiac function is a standard, well characterized model by which the effects of cellular therapies on cardiac function are assessed (Müller-Ehmsen, J. et al., *Circulation* 105:1720-1726 (2002)). After baseline measurements, rats were placed in one of three treatment groups outlined in Table 1.

TABLE 1

| Group | Treatment | No. Animals | Duration of Treatment |
|---|---|---|---|
| Vehicle | 100 µL | 7 Males 7 Females | 4 weeks |
| Unmodified Cells | $5 \times 10^6$ hABM-SCs/100 µL | 7 Males 7 Females | 4 weeks |
| Early-Myocytic Determined Cells | $5 \times 10^6$ hABM-SCs/100 µL | 7 Males 7 Females | 4 weeks |

The early-myocytic determined cells, unmodified cells or vehicle (4.5% glucose in PBS) was delivered to the heart using a 100 µL Hamilton syringe fitted with a 30 gauge, low dead-space needle. The dose of early-myocytic determined cells or unmodified cells was five (5) injections of 20 µl of PBS/4.5% glucose containing $1 \times 10^6$ cells (total $5 \times 10^6$ cells in 100 µl PBS/4.5% glucose). Five separate injections of 20 µL were performed over the course of 2-3 minutes. Four injections were performed at equal distances around the visualized infarct, while the fifth was placed directly into the center of the region with the infarction as determined by area of discoloration indicative of the infarction. After injection, the incision was sutured shut, the pneumothorax was reduced, and the animals were weaned from the respirator and extubated. The rats were returned to their cages upon gaining consciousness. Daily clinical observations were noted for the remaining duration of the study.

Four weeks after injection (5 weeks post-infarction), animals were re-anesthetized, the heart was exposed through a midline sternotomy, and a Millar catheter was inserted. Dp/dt measurements were taken as described above, after which the rats were euthanized via exsanguination. The hearts were harvested, immersion fixed, paraffin embedded, sectioned, stained with hemotoxylin/eosin (H&E) and Trichrome and analyzed histologically with the aid of a light microscope.

Data were blind analyzed by a third party.

Data are expressed as a mean±standard error of the mean (SEM). Statistically significant differences in mean values was determined by Analysis of Variance (ANOVA).
Results Treatment with either modified cells or unmodified cells resulted in significant improvements in several metrics of cardiac function 4 weeks after treatment when compared to vehicle treated control infarcted rats. Histological analysis of cardiac tissue supports the functional data.

Figure 7A:
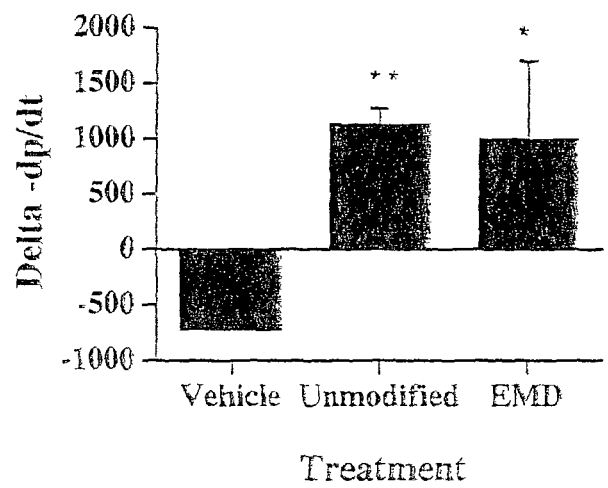
FIGS. 7A and 7B depict the effects of treatment with early-myocytic determined cells (EMD) and unmodified cells on cardiac function in rats following experimental induction of myocardial infarction as measured by peak negative rate of pressure change (-dp/dt). (*$p<0.05$, **$p<0.01$ by ANOVA).
Figure 7B:
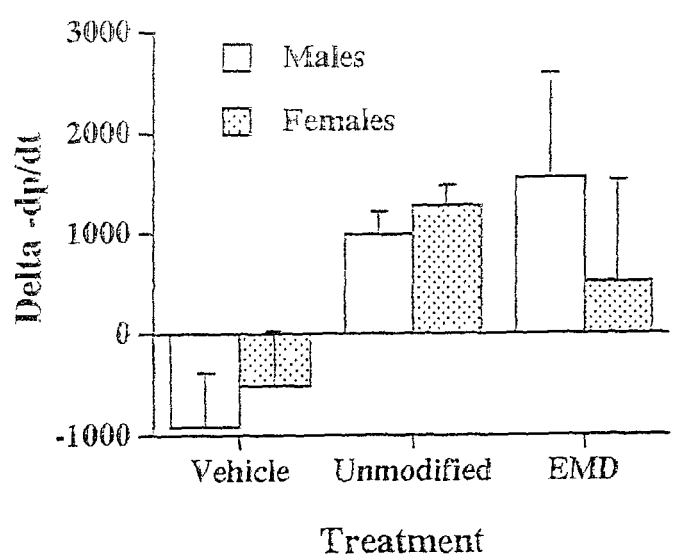
Figure 8A:
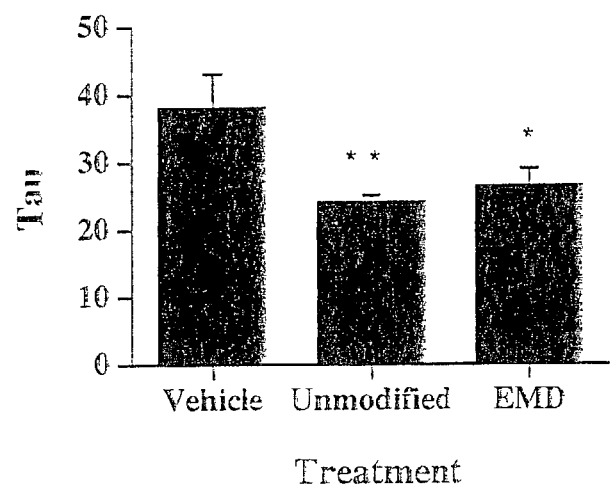
FIGS. 8A and 8B depicts the effects of unmodified cells and early-myocytic determined cells (EMD) on cardiac function in rats following experimental induction of myocardial infarction as measured by the time constant of isovolumetric left ventricular pressure decay (tau). (*p<0.05, **p<0.01 by ANOVA).
Figure 8B:
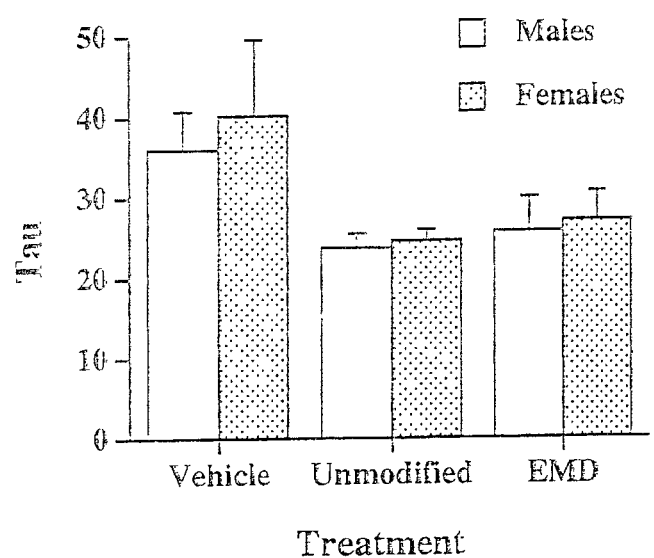

Functional Measurements of Cardiac Tissue:

Statistical analyses was performed on functional data. Due to deaths of some rats at treatment time, as well as the loss of two post-treatment data files, functional data for 6 animals/sex/treatment group was generated. Functional data was analyzed as the following metrics: +dp/dt (FIGS. 6A and 6B), delta +dp/dt (FIGS. 6C and 6D), delta −dp/dt (FIGS. 7A and 7B) and as tau (FIGS. 8A and 8B).

Figure 6A:
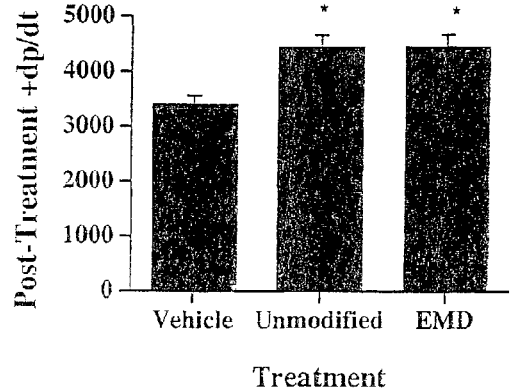
FIG. 6A depicts the effects of early-myocytic determined cells (EMD) and unmodified cells on cardiac function following experimental induction of myocardial infarction as measured by peak positive rate of pressure change (+dp/dt). Four weeks after treatment, rats receiving either unmodified cells or early-myocytic determined cells had significantly higher +dp/dt values. (*$p<0.05$ by ANOVA).

As shown in FIG. 6A, treatment with unmodified cells and modified cells resulted in a significant increase in the maximum rate of pressure development (+dp/dt) 4 weeks after injection. Pretreatment values were not significantly different between groups.

Figure 6B:
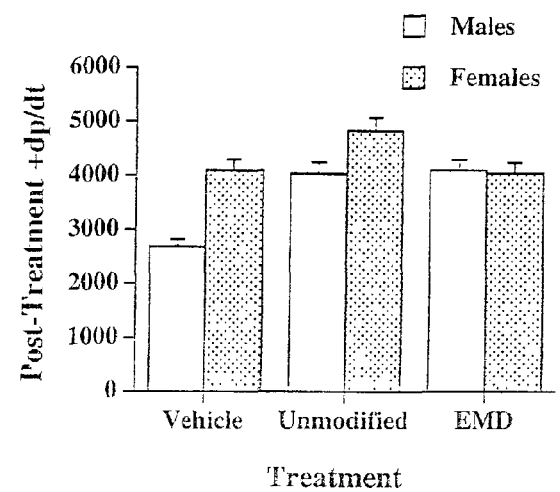
FIG. 6B depicts gender differences in male and female rats following experimental induction of myocardial infarction and treatment with early-myocytic determined cells (EMD) and unmodified cells. (*$p<0.05$ by ANOVA).

As shown in FIG. 6B, vehicle treated males had a significantly lower +dp/dt value when compared to females. However, the degree of increase relative to vehicle was about equal in males and females and less in rats treated with modified cells.

Figure 6C:
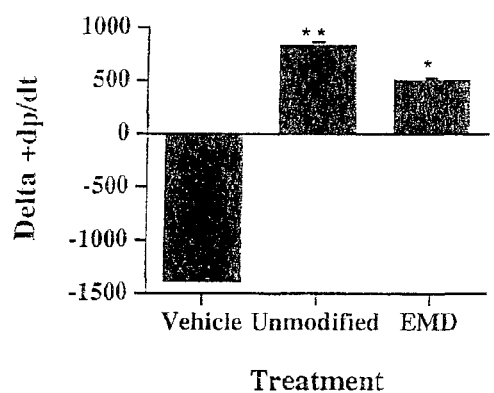
FIG. 6C depicts changes in cardiac function over the course of treatment by subtracting 0 week +dp/dt values from 4 week +dp/dt values to derive a "delta +dp/dt" in rats following experimental induction of myocardial infarction and treatment with early-myocytic determined cells (EMD) or unmodified cells. (*$p<0.05$, **$p<0.01$ by ANOVA).

As a final confirmation that improvements in +dp/dt measurements were of significance, a metric referred to as "delta +dp/dt" was derived. Delta +dp/dt is the absolute change between pretreatment and post-treatment +dp/dt values taken on each individual animal and averaged by the value of the treatment group (FIG. 6C). Delta +dp/dt measurements show that while vehicle animals demonstrated a decrease in this metric (negative delta which indicates decreased cardiac function) during the course of the study, animals receiving either modified cells or unmodified cells demonstrated a significant increase in cardiac function (positive delta which indicates increased cardiac function) as defined by pressure generation metrics.

Figure 6D:
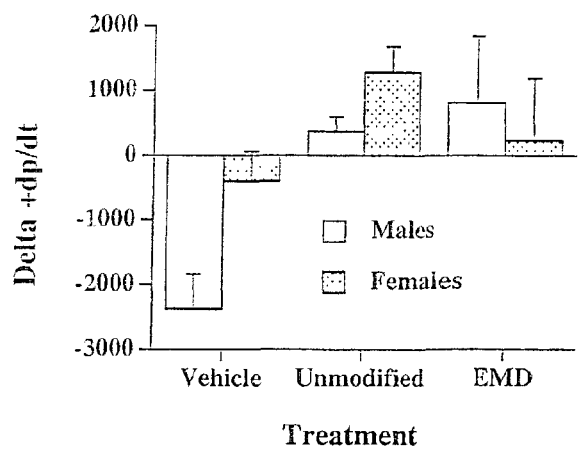
FIG. 6D depicts gender differences in male and female rats following experimental induction of myocardial infarction and treatment with early-myocytic determined cells (EMD) and unmodified cells. (*$p<0.05$, **$p<0.01$ by ANOVA).

As shown in FIG. 6D, males treated with vehicle had a greater decrease in cardiac function (negative delta) when compared to females treated with vehicle. However, males and females demonstrated equivalent increases (positive delta) after treatment with modified cells or unmodified cells.

The minimum rate of pressure development ("−dp/dt") was also determined. A similar analyses as described for +dp/dt was performed (FIGS. 7A and 7B). Results are expressed as "delta −dp/dt," although a similar pattern for pre- and post-treatment measurements was observed. Four weeks after treatment, rats receiving either unmodified cells or modified cells demonstrated significantly higher −dp/dt values (not shown). Unlike +dp/dt values, no differences in −dp/dt were observed between male and female rats.

As shown in FIG. 7A, the delta −dp/dt decreased in vehicle treated animals. However, animals receiving either modified cells or unmodified cells demonstrated significant and robust increases in cardiac function as defined by delta −dp/dt. FIG. 7A shows that expressing changes in cardiac function over the course of the study by subtracting 0 week +dp/dt values from 4 week +dp/dt values ("delta −dp/dt") demonstrated that while vehicle-treated rats had decreases in cardiac function over the course of the study (negative delta), animals treated with either modified cells or unmodified cells showed significant improvements in cardiac function. Unlike +dp/dt, there were no significant differences in the response between males and females (FIG. 7B).

A third metric obtained in this study was the time constant of isovolumetric left ventricular pressure decay, termed tau (t) (FIGS. 8A and 8B). Elevated tau values have been reported in a number of cardiac pathologies in man, including coronary artery disease, myocardial infarct, and diastolic heart failure and, thus, are an index of cardiac function (Bolognesi, R., et al., *J. Am. Soc. Echocardiogr.* 14(8):764-72 (2001); Dawso, J. R., et al., *Br. Heart J.* 61(3):248-257

(1989)). Consistent with the +dp/dt and −dp/dt measurement, rats receiving either modified cells or unmodified cells demonstrated a decreased tau value 4 weeks after treatment (FIG. 8A), suggesting increased left ventricular compliance. As observed with +dp/dt, vehicle treated males tended toward greater decreases in tau over the course of the study, but both sexes demonstrated equal degrees of recovery in tau in response to both test articles when normalized to respective vehicle control (FIG. 8B).

Histological Analysis Cardiac Tissue:

Sections of hearts were stained with H&E and Trichrome. Trichrome staining allows for the visualization of collagen versus muscle tissue. Since collagen can indicate the presence of scar tissue and, thus, the absence of regeneration, H&E and Trichrome staining can be useful to quantify the relative amounts of collagen in cardiac tissue obtained from animals in the experimental treatment groups (vehicle, unmodified cells, early myocytic determined cells) compared to normal cardiac muscle. The scale depicted in Table 2 was employed to correlate quantitative functional data with histological analysis.

TABLE 2

| Scale | Fibrotic/Viable Tissue Area (AF:AV) |
|---|---|
| 0 | Very little |
| 1 | Little |
| 2 | Mild |
| 3 | Moderate |
| 4 | Large |
| 5 | Very Large |

Figure 10A:
FIGS. 10A and 10B are H & E and trichrome staining of cardiac tissue sections obtained from rats following experimental induction of myocardial infarction and subsequent treatment with vehicle (FIG. 10A) or unmodified cells (FIG. 10B). The white line depicts the area of the myocardial infarction.
Figure 10B:
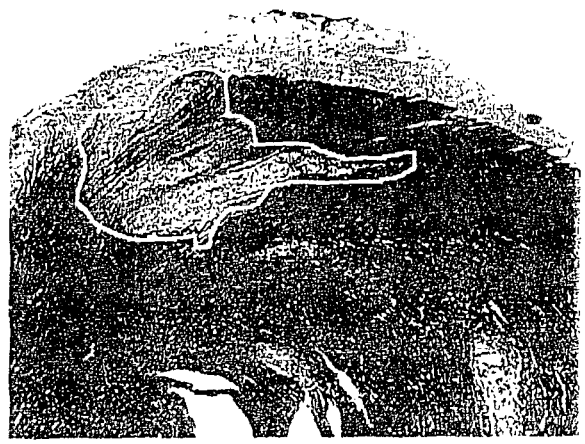

FIGS. 10A and 10B illustrate the relative differences between a vehicle treated rat (FIG. 10A, Score 4) and a rat treated with unmodified cells (FIG. 10B, Score 1). The scores were obtained following visual inspection of three slides of cardiac tissue, starting from the cardiac apex, with each section about 4 mm apart. The score was rendered based upon an average across the three regions of the heart.

A score of 0 was characterized by little to no fibrosis from the apex of the heart to the atrium in cardiac tissue. A score of 1 was characterized by little fibrosis at the apex of the heart and small amounts of fibrous towards to the atrium. A score of 2 was characterized by mild fibrosis at the apex of the heart and quick decreases in the ratio of fibrotic:viable tissue towards the atrium in cardiac tissue. A score of 3 was characterized by moderate fibrosis at the apex of the heart and quick decreases in the ratio of fibrotic:viable tissue towards the atrium in cardiac tissue. A score of 4 was characterized by large fibrosis at the apex of the heart and less rapid decreases in the ratio of mild to fibrotic:viable tissue towards the atrium in cardiac tissue. A score of 5 was characterized by very large fibrosis at the apex of the heart and linear decreases in the ration of fibrotic:viable tissue towards the atrium in cardiac tissue.

The mean score obtained from rats treated with vehicle alone was (4.4±0.68). The mean score obtained from rats treated with modified (1.33±0.68) or unmodified cells (1.00±0.45). For visual representation of a score of 4 and 1, refer to FIGS. 10A and 10B, respectively.

Figure 9:
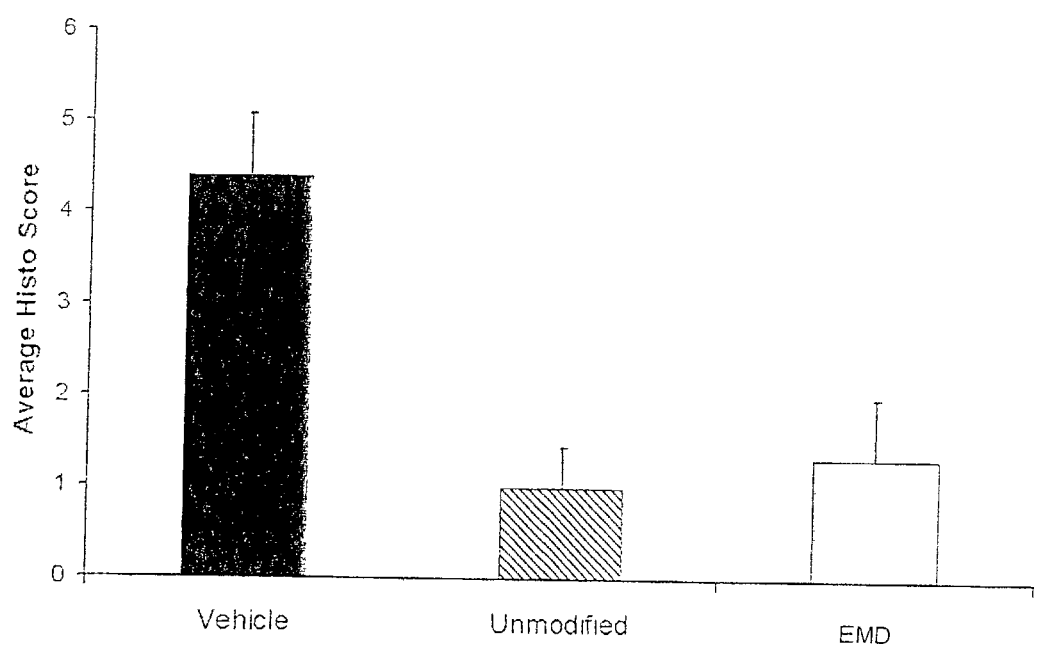
FIG. 9 depicts the histological score (fibrotic/viable tissue area) in cardiac muscle obtained from rats following experimental induction of myocardial infarction and subsequent treatment with unmodified cells or early-myocytic determined cells (EMD).

These data show that a significant reduction in infarct size was observed in rats treated with early-myocytic determined cells and unmodified cells. Generally, infarct size in females was smaller than in males. Rats treated with early-myocytic determined cells or unmodified cells had histological scores approximately two points lower than matched gender vehicle controls (FIGS. 9, 10A and 10B).

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:

1. An isolated cell population induced to express at least one cardiac-related transcription factor, wherein the cell population is derived from bone marrow, wherein greater than about 91% of the cells of the cell population co-express CD49c and CD90, and wherein the cell population is capable of maintaining a doubling rate of less than about 30 hours after 30 cell doublings.

2. The isolated cell population of claim 1, wherein the cells of the cell population that co-express CD49c and CD90 further co-express telomerase.

3. The isolated cell population of claim 1, wherein the bone marrow is human bone marrow.

4. The isolated cell population of claim 1, wherein the cardiac-related transcription factor is selected from the group consisting of GATA4, Irx4 and Nkx2.5.

5. The isolated cell population of claim 1, further including a label.

6. The isolated cell population of claim 1, wherein the cells of the cell population that co-express CD49c and CD90 differentiate into cardiac muscle cells.

7. The isolated cell population of claim 1, wherein the cells of the cell population that co-express CD49c and CD90 further express at least one trophic factor selected from the group consisting of:
   i) brain-derived neurotrophic factor (BDNF)
   ii) nerve growth factor (NGF)
   iii) neurotrophin-3 (NT-3)
   iv) interleukin-6 (IL-6)
   v) interleukin-7 (IL-7)
   vi) interleukin-11 (IL-11)
   vii) stem cell factor (SCF)
   viii) macrophage chemoattractant protein-1 (MCP-1)
   ix) matrix metalloproteinase-9 (MMP-9)
   x) cystatin-C; and,
   xi) vascular endothelial growth factor (VEGF).

8. An isolated cell population induced to express at least one cardiac-related transcription factor, wherein the cell population is derived from bone marrow, wherein greater than about 91% of the cells of the cell population co-express CD49c and CD90, but does not express bone sialoprotein, and wherein the cell population is capable of maintaining a doubling rate of less than about 30 hours after 30 cell doublings.

9. The isolated cell population of claim 8, wherein the cardiac-related transcription factor is selected from the group consisting of GATA4, Irx4 and Nkx2.5.

10. An isolated cell population induced to express GATA4, Irx4 and Nkx2.5, wherein the cell population is derived from bone marrow, wherein greater than about 91% of the cells of the cell population co-express CD49c and CD90, and wherein the cell population is capable of maintaining a doubling rate of less than about 30 hours after 30 cell doublings.

11. An isolated cell population induced to express GATA4, Irx4 and Nkx2.5, wherein the cell population is derived from bone marrow, wherein greater than about 91% of the cells of the cell population co-express CD49c, CD90, and telomerase, and wherein the cell population is capable of maintaining a doubling rate of less than about 30 hours after 30 cell doublings.

12. A pharmaceutical composition comprising an isolated cell population induced to express at least one cardiac-related transcription factor, wherein the cell population is derived from bone marrow, wherein greater than about 91% of the cells of the cell population co-express CD49c and CD90, and wherein the cell population is capable of maintaining a doubling rate of less than about 30 hours after 30 cell doublings.

13. A pharmaceutical composition comprising an isolated cell population induced to express at least one cardiac-related transcription factor, wherein the cell population is derived from bone marrow, wherein greater than about 91% of the cells of the cell population co-express CD49c, CD90, and telomerase, and wherein the cell population is capable of maintaining a doubling rate of less than about 30 hours after 30 cell doublings.

14. A pharmaceutical composition comprising an isolated cell population induced to express GATA4, Irx4 and Nkx2.5, wherein the cell population is derived from bone marrow, wherein greater than about 91% of the cells of the cell population co-express CD49c, CD90, and telomerase, and wherein the cell population is capable of maintaining a doubling rate of less than about 30 hours after 30 cell doublings.

15. A pharmaceutical composition comprising an isolated cell population induced to express GATA4, Irx4 and Nkx2.5, wherein the cell population is derived from bone marrow, wherein greater than about 91% of the cells of the cell population co-express CD49c and CD90, and wherein the cell population is capable of maintaining a doubling rate of less than about 30 hours after 30 cell doublings.

16. An isolated cell population obtainable from human bone marrow and induced to express at least one cardiac-related transcription factor by steps that comprise:
   a) incubating human bone marrow cells under a low oxygen condition such that said cells when allowed to adhere to a tissue culture-treated surface will produce adherent colony forming units (CFU);
   b) passaging cells in said adherent CFU at a seeding density of less than about 2500 cells/cm$^2$; and,
   c) treating the passaged cells with a protein kinase C inhibitor and a DNA methylation inhibitor wherein greater than about 91% of said passaged cells co-express CD49c and CD90, and wherein said passaged cells maintain a population doubling rate of less than about 30 hours after 30 cell doublings.

* * * * *

SEQUENCE LISTING

```
<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide primers

<400> SEQUENCE: 1
atggggatcg gggattgca                                                   19

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primers

<400> SEQUENCE: 2
ccgatccgag ggcctcacta                                                  20

<210> SEQ ID NO 3
<211> LENGTH: 26
<212> TYPE: DNA
```

```
<213> ORGANISM: Artificial Sequence
<220> FEATURE:
<223> OTHER INFORMATION: Oligonucleotide primers

<400> SEQUENCE: 3
cactccagtt gtccccacag tagaca                                          26

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide primers

<400> SEQUENCE: 4
tcgctttcca tgtgtgaggt ga                                              22

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primers

<400> SEQUENCE: 5
ggccggagtg gacgaggcaa                                                 20

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide primers

<400> SEQUENCE: 6
catcaagctt ctgtctgtgc cttctg                                          26

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide primers

<400> SEQUENCE: 7
accgaggcac tcagaggagg c                                               21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide primers

<400> SEQUENCE: 8
gccattagcg catcacagtc g                                               21

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primers

<400> SEQUENCE: 9
gatgttttgc caactggcca agacc                                           25
```

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide primers

<400> SEQUENCE: 10
aggaggggcc agaccatcgc tatct                                    25

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide primers

<400> SEQUENCE: 11
acaacgaacg ccgcttcctc aggaac                                   26

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide primers

<400> SEQUENCE: 12
gccggaacac agccaacccc tgg                                      23

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide primers

<400> SEQUENCE: 13
ggcagctaca gcatgatgca ggacc                                    25

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide primers

<400> SEQUENCE: 14
ctggtcatgg agttgtactg cagg                                     24

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primers

<400> SEQUENCE: 15
caagatggtg actcgaacga                                          20

<210> SEQ ID NO 16
<211> LENGTH: 20
<212> TYPE: DNA
<213> ORGANISM: Artificial Sequence
<220> FEATURE:

```
<223> OTHER INFORMATION: Oligonucleotide primers

<400> SEQUENCE: 16
ggttttgtca aacatcagca                                              20
```